US010564237B2

(12) United States Patent
Bashyam et al.

(10) Patent No.: US 10,564,237 B2
(45) Date of Patent: Feb. 18, 2020

(54) SINGLE-SIDED MAGNETS FOR REMOTE NUCLEAR MAGNETIC RESONANCE MEASUREMENTS

(71) Applicant: Massachusetts Institute of Technology, Cambridge, MA (US)

(72) Inventors: Ashvin Bashyam, Austin, TX (US); Michael J. Cima, Winchester, MA (US); Matthew Li, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 142 days.

(21) Appl. No.: 15/957,429

(22) Filed: Apr. 19, 2018

(65) Prior Publication Data

US 2018/0306879 A1    Oct. 25, 2018

Related U.S. Application Data

(60) Provisional application No. 62/488,343, filed on Apr. 21, 2017.

(51) Int. Cl.
*G01R 33/38* (2006.01)
*A61B 5/055* (2006.01)
*G01R 33/383* (2006.01)

(52) U.S. Cl.
CPC .......... *G01R 33/3808* (2013.01); *A61B 5/055* (2013.01); *G01R 33/383* (2013.01)

(58) Field of Classification Search
CPC .... G01R 33/3808; G01R 33/383; A61B 5/055
See application file for complete search history.

(56) References Cited

U.S. PATENT DOCUMENTS

| 4,844,072 A | 7/1989 | French et al. |
| 5,488,342 A | 1/1996 | Hanley |
| 5,572,132 A | 11/1996 | Pulyer et al. |

(Continued)

FOREIGN PATENT DOCUMENTS

FR    2609556 A1 *  7/1988  ........... A63B 29/021

OTHER PUBLICATIONS

Bashyam et al.; Design and experimental validation of Unilateral Linear Halbach magnet arrays for single-sided magnetic resonance. Feb. 2018, 29 Pages.

(Continued)

*Primary Examiner* — Susan S Lee
(74) *Attorney, Agent, or Firm* — Daly, Crowley, Mofford & Durkee LLP

(57) ABSTRACT

A Unilateral Linear Halbach magnet configuration includes a central magnetized region recessed relative to adjacent magnetized regions disposed on opposite sides of the central magnetized region. The Unilateral Linear Halbach magnet configuration further includes side (or outer) magnetized regions disposed adjacent the center-adjacent magnetized regions. The center and center-adjacent magnetized regions have like-pointing magnetization vectors while the magnetization vectors of the side magnetized regions point in directions orthogonal to the magnetization vectors of the center and center-adjacent regions. Further, the magnetization vectors of the side magnetized regions point in opposite directions.

24 Claims, 18 Drawing Sheets

(56) References Cited

U.S. PATENT DOCUMENTS

| | | |
|---|---|---|
| 6,489,872 B1 | 12/2002 | Fukushima et al. |
| 2015/0091680 A1 | 4/2015 | Gery |
| 2016/0111948 A1 | 4/2016 | Sun et al. |

OTHER PUBLICATIONS

Bashyam et al.; Portable single-sided MR: multicomponent T2 relaxometry and depth profiling with a Unilateral Linear Halbach sensor. Nov. 8, 2017; 4 pages.

Bloch; Nuclear Induction. Phys. Rev.; vol. 70; Oct. 1, 1946; 15 pages.

Bloembergen et al.; Relaxation Effects in Nuclear Magnetic Resonance Absorption. Phys. Rev.; vol. 73; Apr. 1, 1948; 37 pages.

Blümich et al.; Advances of unilateral mobile NMR in nondestructive materials testing. Mag. Res. Imaging; vol. 23; Jan. 1, 2005; 5 pages.

Blümich et al.; Simple NMR-MOUSE with a Bar Magnet Magn. Reson. Engineering; vol. 15; Jul. 25, 2002; 7 pages.

Casanova et al.; Single-Sided NMR. *Single-Sided NMR*, Springer-Verlag Berlin Heidelberg; Jan. 1, 2011; 254 pages.

Chang et al. Single-sided mobile NMR with a Halbach Magnet. Mag Res Imagine; vol. 24; Feb. 15, 2006; 8 pages.

Chizhik et al.; Magnetic Resonance and Its Applications. Springer International Publishing Switzerland. Jan. 1, 2014. Part 1, 200 pages.

Chizhik et al.; Magnetic Resonance and Its Applications. Springer International Publishing Switzerland. Jan. 1, 2014. Part 2, 200 pages.

Chizhik et al.; Magnetic Resonance and Its Applications. Springer International Publishing Switzerland. Jan. 1, 2014. Part 3, 200 pages.

Chizhik et al.; Magnetic Resonance and Its Applications. Springer International Publishing Switzerland. Jan. 1, 2014. Part 1, 185 pages.

Demas et al.; Compact Magnets for Magnetic Resonance. Concepts Magn Reson. Received Sep. 5, 2008; 12 pages.

Eidmann et al.; The NMR MOUSE, a Mobile Universal Surface Explorer. J. Magn. Res. Series A 122; Jul. 1, 1996. 6 pages.

Freude et al.; Quadrupole Effects in Solid-State Nuclear Magnetic Resonance. ResearchGate Publication; Jan. 1, 1993. 47 pages.

Gottvald et al.; Optimal Magnet Design for NMR. IEEE Trans. on Magn. vol. 26; Mar. 1, 1990. 4 pages.

Guthausen et al.; Measurement of Fat Content of Food with Single Sided NMR. JAOCS; vol. 81; Aug. 1, 2004. 6 pages.

Halbach et al.; Design of Permanent Multipole Magnets with Oriented Rare Earth Cobalt Materials. Nucl. Inst and Meth; vol. 169; Jan. 1, 1980. 12 pages.

Hoult et al.; The Signal-to-Noise Ratio of the Nuclear Magnetic Resonance Experiment. J. Magn. Res.; vol. 24; Mar. 5, 1976. 15 pages.

Kobzar et al.; Exploring the limits of broadband excitation and inversion pulses. J. Magn. Res.; vol. 170; Apr. 3, 2004. 8 pages.

Kornetka et al.; Evaluation of a mobile NMR sensor for determining skin layers and locally estimating the T2eff relaxation time in the lower arm. Magn. Reson. Mater. Phys. vol. 25; Apr. 18, 2012. 13 pages.

Mallinson. One-Sided Fluxes—A Magnetic Curiosity? IEEE Trans. On Magn. vol. MAG-9. Dec. 1, 1973. 5 pages.

Marble et al.; A compact permanent magnet array with a remote homogeneous field. J. Magn. Res. vol. 186; Jan. 26, 2007. 5 pages.

Parker et al.; Shimming Halbach magnets utilizing genetic algorithms to profit from material imperfections. J. Magn. Res. vol. 265; Jan. 14, 2016. 7 pages.

Prado et al.; One-Dimensional Imaging with a Palm Size Probe. J. Magn. Res. vol. 144; Jul. 9, 1999. 7 pages.

Pulyer et al.; Generation of Remote Homogeneous Magnetic Fields. IEEE Trans. On Magn. vol. 38; May 1, 2002. 11 pages.

Tayler et al.; Low-cost, pseudo-Halbach dipole magnets for NMR. J. Magn. Res. vol. 277; Feb. 7, 2017. 6 pages.

Utsuzawa et al.; Unilateral NMR with a barrel magnet. J. Magn. Res. vol. 282; Jun. 25, 2017. 10 pages.

Van Landeghem et al.; Low-gradient single-sided NMR sensor for one-shot profiling of human skin. J. Magn. Res. vol. 215; Jul. 25, 2011. 11 pages.

Vassiliou. Biopsy-Implantable Chemical Sensor. Submitted to the Dept. of Electrical Eng. And Computer Science on Aug. 30, 2013. 198 pages.

International Preliminary Report on Patentability dated Oct. 31, 2019 for International Application No. PCT/US2018/028522; 8 Pages.

PCT International Search Report dated Oct. 17, 2018, for Application No. PCT/US2018/028522; 7 Pages.

PCT Written Opinion of the International Searching Authority dated Oct. 17, 2018, for Application No. PCT/US2018/028522; 9 Pages.

Bashyam; "Nuclear Magnetic Resonance Sensors and Methods for Chemical Sensing in Tissue"; MIT Libraries, Chapters 1.3, 3 and 5; Jul. 12, 2016; pp. 1-107; 107 Pages.

Bashyam; "Nuclear Magnetic Resonance Sensors and Methods for Chemical Sensing in Tissue"; MIT; Dec. 5, 2016; 3 Pages.

Bashyam, et al.; "Unilateral Linear Halbach Magnets for Single Sided Magnetic Resonance: Generalized Design Framework and Experimental Validation"; International Society for Magnetic Resonance in Medicine, ISMRM; Apr. 7, 2017; pp. 1-4; 4 Pages.

Bashyam, et al.; Design and Experimental Validation of Unilateral Linear Halbach Magnet Arrays for Single-Sided Magnetic Resonance; Journal of Magnetic Resonance; vol. 292; Jul. 1, 2018; pp. 36-43; 8 Pages.

* cited by examiner

SINGLE-SIDED MAGNETS FOR REMOTE NUCLEAR MAGNETIC RESONANCE MEASUREMENTS

CROSS-REFERENCE TO RELATED APPLICATIONS

This application claims benefit of U.S. Provisional Application No. 62/488,343, filed on Apr. 21, 2017, which is hereby incorporated in its entirety.

STATEMENT REGARDING FEDERALLY SPONSORED RESEARCH

This invention was made with Government Support under Grant No. W911NF-13-D-0001 awarded by the Army Research Office. The government has certain rights in the invention.

FIELD

The concepts, systems, configurations, devices and techniques described herein relate generally to nuclear magnetic resonance and more particularly, to a magnet array configuration and associated control techniques for use in nuclear magnetic resonance applications.

BACKGROUND

As is known in the art, single-sided nuclear magnetic resonance ("NMR") has the potential for use in a wide variety of different applications. For example, single-sided NMR sensors may find use as a portable diagnostic for disorders in fluid regulation. Such sensors require a remote, uniform magnetic field to achieve sufficient sensitivity.

Maintenance of fluid balance in the body is critical to physical and cognitive function yet no accurate, robust, and practical assessment method currently exists. Proper fluid management is necessary for renal and heart failure patients, competitive athletes, soldiers, and the elderly. Current approaches rely on indirect measures that are subject to significant variability during physician interpretation or invasive measures that cannot be routinely performed. These methods include blood and urine chemistry, bioimpedance, and even radioisotope dilution. All are either invasive, require a lab, or have proven to be not clinically reliable. Thousands of medical errors and billions of dollars of unnecessary expenditure occur annually due to improper fluid management in the US.

Proton nuclear magnetic resonance (1H NMR) relaxometry provides a direct measure of water volumes and concentration. The nucleic specificity of MR intrinsically measures only signal from water, which vastly improves sensitivity compared to other, easily confounded diagnostic methods. Magnetic resonance imaging (MRI), a specialized form of NMR, can measure fluid levels, but is highly impractical for routine diagnostic use due to extended measurement times, high cost, and limited availability.

Measurement of the fluid distribution in lean muscle tissue offers potential in managing fluid disorders such as dehydration and volume overload. However, accessing this tissue for measurement requires that the measurement penetrate beneath superficial tissue layers—such as, for example, the epidermis, dermis, or subcutaneous tissue layers. The ability of single-sided NMR systems to interrogate tissue remote to the surface of the sensor enables measurements of anatomical regions previously not possible with closed bore systems. Single-sided NMR relies on the existence of a remote uniform magnetic field. Ideally, the field lines of the homogenous region are parallel to the surface of the magnet to allow for the use of standard surface coils for radio frequency (RF) excitation and signal acquisition. A magnetic field with a large, high field strength uniform region is required for high sensitivity measurements.

It would, therefore, be desirable to provide a magnet geometry capable of providing a magnetic field having a high field strength and which is relatively homogeneous over a large region.

SUMMARY

Described are concepts, systems, and techniques directed toward a magnet configuration referred to herein as a Unilateral Linear Halbach configuration. A magnet or array of magnets arranged in a Unilateral Linear Halbach configuration provides a magnetic field having a desired field strength over a desired region. A Unilateral Linear Halbach magnet configuration more efficiently utilizes magnetic mass and enables precise specification of the depth and size of a uniform magnetic field. Thus, compared with prior art magnet or magnet array configurations, for a given magnetic mass, the magnetic field strength and size of a region over which the magnetic field is homogenous achieved with a Unilateral Linear Halbach magnet array configuration is larger than that achieved by prior art magnets or magnet array configurations.

A sensor utilizing a Unilateral Linear Halbach magnet configuration is capable of performing deep measurements (i.e. measurements which penetrate beneath superficial tissue layers, such as, for example, a subcutaneous layer of a person) useful in applications such as predicting and monitoring fluid dysregulation disorders.

In accordance with a still further aspect of the concepts, systems, and techniques described herein, a nuclear magnetic resonance (NMR) system comprising a Unilateral Halbach array, may be used in applications including, but not limited to: (1) a tool (or device) to routinely check for congestive heart failure (CHF); (2) detection of volume depletion (e.g. dehydration in military, elderly, athletes); (3) monitoring of dialysis in kidney failure patients; (4) measurement of vascular volume and perturbations, such as hemodilution from fluid intake; (5) diagnosis and prognosis of muscle atrophy induced by, for example, denervation, degenerative diseases, or disuse; (5) measurement of fatty infiltration and/or fibrosis in vital organs—such as the liver in the case of steatohepatitis and/or steatosis, or any combination thereof.

In accordance with a still further aspect of the concepts, systems, and techniques described herein, a magnet assembly includes a first center-adjacent magnet having a magnetization poles oriented in a first direction and having a first surface, a second center-adjacent magnet spaced apart from said first magnet, said second magnet having a magnetization pole oriented in the first direction and having a first surface, at least one center magnet disposed in the space between the first and second center-adjacent magnets, said center magnet having a magnetization pole oriented in the first direction and having a first surface offset from the first surfaces of the first and second center-adjacent magnets and being arranged symmetrically with respect to a central longitudinal axis of the magnet assembly, a first outer magnet having a first surface, said first outer magnet disposed away from the central longitudinal axis in the direction of the magnetization vectors of the first and second center-adjacent magnets and proximate the first center-adjacent magnet, said first outer magnet having a magnetization vector directed in a direction which is orthogonal to a direction of the magnetization vectors of the first center-adjacent magnet and pointed in the direction of the first surface of the first center-adjacent magnet and a second outer magnet having a first surface, said second outer magnet disposed proximate the second center-adjacent magnet, said second outer magnet having a magnetization vector directed in a direction which is orthogonal to the direction of the magnetization vectors of the second center-adjacent magnet and which is in a direction which is opposite the direction of the magnetization vector of said first outer magnet whereby the first and second center-adjacent magnets and first and second outer magnets generate a substantially uniform magnetic field of sufficient strength to perform a nuclear magnetic resonance (NMR) process in a working region above the first surfaces of the first center-adjacent, second center-adjacent and center magnets.

In embodiments, the first surfaces of the first and second center-adjacent magnets are substantially aligned a single plane.

In embodiments, the first surfaces of the first and second outer magnets are substantially aligned a single plane.

In embodiments, the first surfaces of the first and second center-adjacent magnets and the first surfaces of the first and second outer magnets are substantially aligned a single plane.

In embodiments, the first center-adjacent magnet is a first one of a plurality of first center-adjacent magnets, with each of said plurality of first center-adjacent magnets disposed in the region of the first center-adjacent magnet so as to form a first center-adjacent slice and each of said plurality of first center-adjacent magnets disposed such that the magnetization vectors are oriented in the same direction as the first center-adjacent magnet; and the second center-adjacent magnet is a first one of a plurality of second center-adjacent magnets, with each of said plurality of second center-adjacent magnets disposed in the region of the second center-adjacent magnet so as to form a second center-adjacent slice and each of said plurality of second center-adjacent magnets disposed such that the magnetization vectors are oriented in the same direction as the second center-adjacent magnet.

In embodiments, the first outer magnet is a first one of a plurality of first outer magnets, with each of said plurality of first outer magnets disposed in the region of the first outer magnet so as to form a first outer slice and each of said plurality of first outer magnets disposed such that the magnetization vectors of the plurality of first outer magnets are oriented in the same direction as the first outer magnet; and the second outer magnet is a first one of a plurality of second outer magnets, with each of said plurality of second outer magnets disposed in the region of the second outer magnet so as to form a second outer slice and each of said plurality of second outer magnets disposed such that the magnetization vector of the plurality of second outer magnets are oriented in the same direction as the second outer magnet.

In embodiments, the first magnets, second magnets and first and second outer magnets are disposed in a housing.

In accordance with a still further aspect of the concepts, systems, and techniques described herein, a magnet assembly, includes a pair of spaced apart first magnets having both magnetization poles oriented in a same direction and having at least one surface substantially aligned in a single plane; at least one second magnet disposed in the space between the first magnets, the at least one second magnet having a surface offset from the single plane and being arranged symmetrically with respect to a central longitudinal axis of the magnet assembly, said pair of spaced apart first magnets and each of said at least one second magnet having magnetization vectors directed in the same direction; a first outer magnet disposed proximate a first one of the pair of spaced apart first magnets, said first outer magnet having at least one surface substantially aligned in a single plane with like surfaces of the pair of spaced apart first magnets and said first outer magnet having a magnetization vector directed in a direction which is orthogonal to a direction of the magnetization vectors of the pair of spaced apart first magnets; a second outer magnet disposed proximate a second one of the pair of spaced apart first magnets, said second outer magnet having at least one surface substantially aligned in the single plane with like surfaces of the pair of spaced apart first magnets and said second outer magnet having a magnetization vector directed in a direction which is orthogonal to the direction of the magnetization vectors of the pair of spaced apart first magnets and which is in a direction which is opposite the direction of the magnetization vector of said first outer magnet whereby the first and second magnets and first and second outer magnets generate a substantially uniform magnetic field of sufficient strength to perform a nuclear magnetic resonance (NMR) process in a working region above at least one of the first and second magnets.

In embodiments, the first outer magnet is adjacent the first one of the pair of spaced apart first magnets. In embodiments, the second outer magnet is adjacent the second one of the pair of spaced apart first magnets.

In embodiments, the first outer magnet is disposed away from the central longitudinal axis in the direction of the magnetization vectors of the pair of spaced apart first magnets.

In embodiments, the first outer magnet has a magnetization vector directed towards the single plane.

In embodiments, the uniform magnetic field is located above a surface of the first and second magnets.

In embodiments, the uniform magnetic field is located above a central region of the first and second magnets.

In embodiments, the first magnets, second magnets, first outer magnets and second outer magnets are disposed in a housing.

In accordance with a still further aspect of the concepts described herein, in a portable measurement device, an array of magnets includes a first magnet having top and bottom surfaces and at least one side surface, a second magnet having top and bottom surfaces and at least one side surface, said second magnet spaced apart from said first magnet with the top surface of said first magnet and the top surface of said second magnet being substantially in a same plane, a third magnet having top and bottom surfaces and at least one side surface, said third magnet disposed between the first and second magnets, such that the top surface of said third magnet is in a plane which is different from the plane in which the top surfaces of said first and second magnets lie wherein the first, second, and third magnets each have magnetization vectors in a same direction and the array of magnets further includes fourth and fifth magnets each having top and bottom surfaces and at least one side surface with the top surfaces of said fourth and fifth magnet and the top surfaces of said first and second magnets being substantially in the same plane, said fourth and fifth magnets having magnetization vectors which are in a direction which is orthogonal to the direction of the magnetization vectors of said first, second and third magnets and wherein the direction of the magnetization vector of the fourth magnet is opposite the direction of the magnetization vector of the fifth magnet.

In embodiments, the fourth magnet is further disposed away from the first magnet in the direction of the magnetization vectors of the first, second, and third magnets.

In embodiments, the fourth magnet has a magnetization vector directed towards the plane in which the top surfaces of the said first and second magnets lie.

In embodiments, the top surface of said third magnet is in a plane which is below a plane in which the top surfaces of said first and second magnets lie.

In embodiments, the first, second, third, fourth and fifth magnets are each provided having a substantially same size and shape.

In embodiments, the first, second, third, fourth, and fifth magnets are configured to provide a uniform magnetic field in a region above the top surface of the first, second and third magnets.

In embodiments, the uniform magnetic field is located above a central region of the first, second, and third magnets.

In embodiments, the first, second, and third magnets each comprise a respective matrix of magnets, wherein each matrix of magnets comprises at least one magnet in an x direction of the matrix and at least one magnet in a y direction of the matrix.

In embodiments, each magnet in the matrix of magnets is provided having effectively a rectangular prism shape.

In accordance with a still further aspect of the concepts, systems, and techniques described herein, a method for measuring according to nuclear magnetic resonance (NMR), includes generating, by a magnet having a Unilateral Linear Halbach geometry, a remote, uniform magnetic field and measuring a volume of a sample to be measured within the generated, remote, uniform magnetic field.

In embodiments, a method may further include determining a state of a liquid within the sample to be measured.

In embodiments, the remote, uniform magnetic field is substantially located above a central region of the magnet.

In embodiments, the magnet comprises at least three magnets substantially parallel with respect to one another.

In embodiments, a top surface of a center one of the three magnets lies in a plane different from top surfaces the two non-center magnets.

In accordance with a still further aspect of the concepts, systems, and techniques described herein, in a portable measurement device, an array of magnets includes a first magnet having first and second opposite opposing ends comprising a first magnetization domain having top and bottom surfaces and at least one side surface, a second magnetization domain having top and bottom surfaces and at least on side surface, said second domain spaced apart from said first domain with the top surface of said first domain and the top surface of said second domain being substantially in a same plane, and a third magnetization domain having top and bottom surfaces and at least one side surface, said third domain disposed between the first and second domains, such that the top surface of said third domain is in a plane which is different from the plane in which the top surfaces of said first and second domains lie wherein each of the first, second, and third domains generate a magnetic field in substantially the same direction. The array of magnets may further include a second magnet having top and bottom surfaces and at least one side surface, said second magnet spaced apart from the first end of the first magnet with the top surface of said second magnetic being in substantially the same plane as the top surfaces of the first and second domains of the first magnet and a third magnet having top and bottom surfaces and at least one side surface, said third magnet space apart from the second end of the first magnet with the top surface of said third magnetic being in substantially the same plane as the top surfaces of the first and second domains of the first magnet wherein each of the second and third magnets generate a magnetic field orthogonal to the magnetic fields generated by the first, second, and third domains of the first magnet and anti-parallel to each other.

In embodiments, the magnetic fields generated by the second and third magnets are anti-parallel.

In accordance with a still further aspect of the concepts, systems, and techniques described herein, in a portable measurement device, an array of magnets includes a magnet having first and second opposite opposing ends comprising: a first discrete magnetization domain having top and bottom surfaces a at least one side surface, a second discrete magnetization domain having top and bottom surfaces and at least on side surface, said second domain spaced apart from said first domain with the top surface of said first domain and the top surface of said second domain being substantially in a same plane, a third discrete magnetization domain having top and bottom surfaces and at least one side surface, said third domain disposed between the first and second domains, such that the top surface of said third domain is in a plane which is different from the plane in which the top surfaces of said first and second domains lie, a fourth discrete magnetization domain having top and bottom surfaces and at least one side surface, said fourth domain disposed at the first end of the magnet spaced apart from the first domain with the top surface of said second magnetic being in substantially the same plane as the top surfaces of the first and second domains of the first magnet, and a fifth discrete magnetization domain having top and bottom surfaces and at least one side surface, said fifth domain disposed at the second end of the magnet spaced apart from the second domain with the top surface of said second magnetic being in substantially the same plane as the top surfaces of the first and second domains of the first magnet wherein each of the first, second, and third domains generate a magnetic field in substantially the same direction and wherein each of fourth and fifth domains generate a magnetic field perpendicular to the magnetic fields generated by the first, second, and third domains of the first magnet.

In accordance with a still further aspect of the concepts, systems, and techniques described herein, in a portable measurement device, an array of magnets configured to provide a remote, substantially uniform magnetic field of sufficient strength to perform a nuclear magnetic resonance (NMR) process comprising a first magnet having top and bottom surfaces, a second magnet having top and bottom surfaces, said second magnet spaced apart from said first magnet with the top surface of said first magnet and the top surface of said second magnet being substantially in a same plane, a third magnet having top and bottom surfaces, said third magnet disposed between the first and second magnets, such that the top surface of said third magnet is in a plane which is different from the plane in which the top surfaces of said first and second magnets lie, a fourth magnet having top and bottom surfaces, said fourth magnet disposed at a first end of the first, second, and third magnets spaced apart from the first magnet, such that the top surface of said fourth magnet being substantially in the same plane in which the top surfaces of the first and second magnets lie; and a fifth magnet having top and bottom surfaces and at least one side surface, said fifth magnet disposed at a second end of the first, second, and third magnets spaced apart from the second magnet, such that the top surface of said fifth magnet being in being substantially in the same plane in which the top surfaces of the first and second magnets lie wherein the first, second, and third magnets each generate a magnetic field in a substantially same direction and wherein the fourth and fifth magnets each generate a magnetic field substantially orthogonal to magnetic fields generated by the first, second, and third magnets.

In embodiments, the first, second, third, fourth, and fifth magnets are substantially parallel to one another.

In embodiments, the magnetic fields generated by the fourth and fifth magnets are anti-parallel to one another.

In embodiments, the magnetic fields generated by the first, second, and third magnets are in a negative direction along an x-axis.

In embodiments, the magnetic field generated by the fourth magnet is in a positive direction along a y-axis perpendicular to the x-axis In embodiments, the magnetic field generated by the fifth magnet is in a negative direction along the y-axis perpendicular to the x-axis.

In embodiments, the first, second, third, fourth, and fifth magnets generate a substantially uniform magnetic field of sufficient strength to perform a nuclear magnetic resonance (NMR) process.

In embodiments, the substantially uniform magnetic field is in a positive direction along the x-axis.

In embodiments, the plane in which the top of the third magnets lies at a height below the plane in which the top of the first and second magnets lie.

In embodiments, the first, second, third, fourth, and fifth magnets are spaced apart by a substantially equal distance.

In embodiments, the first, second, third, fourth, and fifth magnetics are disposed within a housing.

In accordance with a still further aspect of the concepts, systems, and techniques described herein, a nuclear magnetic resonance (NMR) system includes a plurality of magnets disposed in a Unilateral Linear Halbach array geometry, wherein the Unilateral Linear Halbach magnet array geometry establishes a remote, uniform magnetic field.

In embodiments, the remote, uniform magnetic field is above a central region of the Unilateral Linear Halbach magnet array.

In embodiments, the remote, uniform magnetic field has an effectively uniform strength between 0.05 to 0.5 Tesla.

In embodiments, the remote, uniform magnetic field has an effectively uniform strength between 0.01 to 0.8 Tesla.

In embodiments, the NMR system is configured to perform a measurement using the uniform magnetic field.

In embodiments, the NMR system is configured to perform a measurement of a volume of tissue based upon the remote, uniform magnetic field.

In embodiments, the NMR system is further configured to determine a distribution of liquid within the tissue.

BRIEF DESCRIPTION OF THE DRAWINGS

The foregoing features may be more fully understood from the following description of the drawings in which.

Figure 1:
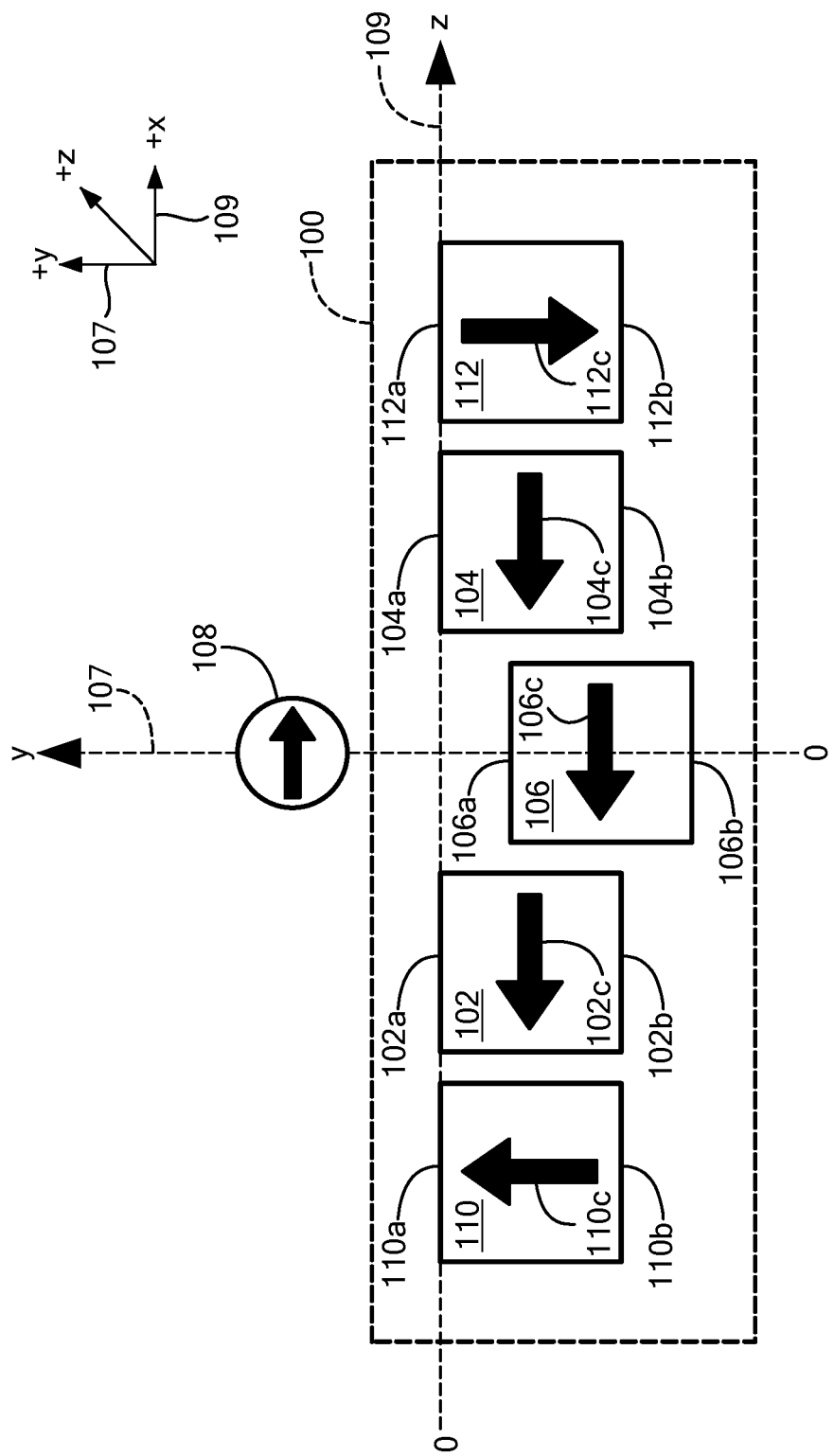
FIG. 1 is a block diagram of a Unilateral Linear Halbach magnet array.

It should be appreciated that the drawings are not necessarily to scale, or inclusive of all elements of a system, emphasis instead generally being placed upon illustrating the concepts, structures, and techniques sought to be protected herein.

DETAILED DESCRIPTION

Before proceeding with a discussion of illustrative embodiments of a magnet configuration referred to herein as a Unilateral Linear Halbach configuration, some introductory concepts and terminology are explained. In general overview, a Unilateral Linear Halbach magnet configuration includes a central magnetized region which is displaced (e.g. recessed) relative to adjacent magnetized regions disposed on opposite sides of the central magnetized region. The Unilateral Linear Halbach magnet configuration further includes outer (or "side" or "external") magnetized regions disposed adjacent the center-adjacent magnetized regions. The center and center-adjacent magnetized regions have magnetization vectors which ideally point in the same direction. In practical systems, however, the magnetization vectors of the center and center-adjacent magnetized regions may be pointed in as close to the same direction as necessary so as to be capable of being used to perform nuclear magnetic resonance ("NMR") measurements). The outer magnetized regions are provided such that their magnetization vectors are pointed in a direction which is substantially orthogonal to the magnetization vectors of the center and center-adjacent magnetized regions. Furthermore, the magnetization vectors of the outer magnetized regions are anti-parallel to each other (again, as antiparallel as is necessary to achieve NMR measurements) and colinear with the direction of the displacement of the central magnetized region ((again, colinear to the extent necessary to achieve NMR measurements). That is, the magnetization vector of a first one of the outer magnetized regions is directed in a direction which is opposite the magnetization vector of a second one of the outer magnetized regions (i.e. the magnetization vectors of the outer magnetized regions are anti-parallel to each other).

Further still, the outer magnetized region which is disposed proximate the center-adjacent regions in the direction of the magnetization vectors of the center and center-adjacent magnetized regions (e.g. the first outer magnetized region) has a magnetization vector that points in a direction opposite of, or anti-parallel to, the direction of displacement of the central magnetization region. The outer magnetized region which is disposed proximate the center-adjacent regions in a direction opposite of the direction of the magnetization vectors of the center and center-adjacent magnetized regions has a magnetization vector that points in a direction which is the same as the direction of displacement of the central magnetization region. Thus, the directions of the magnetization vectors of the center, center-adjacent and outer magnets are provided having a particular relationship with respect to each other.

In the description hereinbelow, illustrative Unilateral Linear Halbach configurations are described in which the central magnetized region, center-adjacent magnetized regions and outer magnetized regions are provided from separate magnets (i.e. the Unilateral Linear Halbach configuration may be provided from an array of individual magnets). Such illustrative embodiments are not intended as, and should not be construed as, limiting.

Indeed, it is fully appreciated that in other embodiments, the Unilateral Linear Halbach configuration may be provided from an array of magnets in which two or more of the center magnetized region, center-adjacent magnetized regions and outer magnetized regions are provided from one or more individual magnets (i.e. a single unitary or integrated magnet having magnetic domains with magnetization vectors which point in appropriately selected directions as noted above and as will be described in further detail herein below).

It is also appreciated that, in embodiments, the central magnetized region, center-adjacent magnetized regions and outer magnetized regions may be provided as magnetized regions of a single unitary or integrated magnetic structure.

It should thus be appreciated that the broad concepts described herein are not limited to any particular implementation details such as a specific arrangement of physical magnets. Rather the broad concepts described herein may be applied to a wide variety of different arrangement of physical magnets while maintaining structural and magnetic relationships to provide a Unilateral Linear Halbach configuration.

It should also be appreciated that relative or directional terms such as above, below, left, right, top, bottom are used only for illustrative purposes and to promote clarity in the description of the figures and are not intended as and should not be construed as limiting. Directions and references (e.g., up, down, top, bottom, left, right, rearward, forward, etc.) may be used to facilitate discussion of the drawings but are not intended to be limiting. For example, certain terms may be used such as "up," "down,", "upper," "lower," "horizontal," "vertical," "left," "right," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" surface can become a "lower" surface simply by turning the object over. Nevertheless, it is still the same surface and the object remains the same. As used herein, "and/or" means "and" or "or", as well as "and" and "or." Moreover, all patent and non-patent literature cited herein is hereby incorporated by references in its entirety for all purposes.

Turning now to FIG. 1, an illustrative embodiment of a magnet array 100 arranged in a Unilateral Linear Halbach configuration includes a plurality of magnets, here five (5) magnets 102, 104, 106, 110, 112. Each of magnets 102, 104, 106, 110, 112 are provided having respective top and bottom surfaces 102a, 102b, 104a, 104b, 106a, 106b, 110a, 110b, 112a, 112b, and least one side surface. Surfaces 102a, 104a, 110a, 112a of center-adjacent and outer magnets 102, 104, 110,112 lie in the same plane. In this illustrative embodiment, center magnet 106 is displaced relative to magnets 102, 104, 110, 112 and thus top surface 106a of center magnet 106 is in a plane which is different than the plane in which lies top surfaces 102a, 104a, 110a, 112a of center-adjacent and outer magnets 102, 104, 110, 112.

The center magnet 106 and center-adjacent magnets 102, 104 have respective magnetization vectors 102c, 104c, 106c which point in the same (or substantially the same) direction. In this illustrative embodiment, the magnetization vectors 102c, 104c, 106c of magnets 102, 104, 106 are directed in the negative Z direction (−Z) as defined by the Cartesian coordinate system of FIG. 1 (i.e. the magnetization vectors 102c, 104c, 106c point to the left in FIG. 1).

It should be appreciated that while in this illustrative embodiment, a single center-adjacent magnet 102 is disposed on a first side of center magnet 106 and a single center-adjacent magnet 104 is disposed adjacent a second, opposite side of center magnet 106, in embodiments, multiple center-adjacent magnets 102, 104 may be disposed on either side of the center magnet 106 (e.g. as shown in FIGS. 2C-2F).

Also, in the illustrative embodiment of FIG. 1, a first outer magnet 110 (also referred to as a "side" or "external" magnet) is disposed next to center-adjacent magnet 102 and a second side (or external) magnet 112 is disposed next to center-adjacent magnet 104. Thus, in the illustrative embodiment of FIG. 1, a single outer magnet 110 is disposed adjacent center-adjacent magnet 102 and a single outer magnet 112 is disposed adjacent center-adjacent magnet 104. It should, of course, be appreciated that in embodiments, multiple outer magnets may be disposed next to each of the center adjacent magnets 102, 104. Examples of such embodiments will be described below in conjunction with FIGS. 2E and 2F.

Significantly, outer magnets 110, 112 are arranged such that a direction of a magnetization vector of each outer magnet is directed (or pointing) in a direction which is substantially orthogonal (i.e. as close to orthogonal as is necessary to achieve NMR measurements) to the direction of the magnetization vector of the center and center-adjacent magnets 106, 102, 104. Furthermore, the magnetization vectors of each outer magnet 110, 112 are anti-parallel. That is, the magnetization vector of outer magnet 110 points in a direction which is opposite (or substantially opposite) the magnetization vector of outer magnet 112. That is, the magnetization vectors of the outer magnets 110, 112 on opposite ends of the array are directed in opposite (or substantially opposite) directions.

In the example of FIG. 1, outer magnet 110 is disposed away from center magnet 106 in the same direction in which magnetization vectors 102c, 104c, and 106c point. That is to say, outer magnet 110 is disposed away from center magnet 106 in the negative Z direction (−Z) as defined by the Cartesian coordinate system of FIG. 1 (i.e. magnet 110 is to the left of magnet 106 FIG. 1). Further, outer magnet 110 has a magnetization vector 110c that points in a direction towards the plane in which lies top surfaces 102a, 104a, 110a,112a of center-adjacent magnets 102, 104. In other words, magnetization vector 110c is directed in the positive Y direction (+Y) as defined by the Cartesian coordinate system of FIG. 1 (i.e. magnetization vector 110c is pointed up in the example of FIG. 1).

Outer magnet 112 is disposed away from center magnet 106 in the direction opposite from (or anti-parallel to) the direction in which magnetization vectors 102c, 104c, and 106c point. That is to say, outer magnet 112 is disposed away from center magnet 106 in the positive Z direction (+Z) as defined by the Cartesian coordinate system of FIG. 1 (i.e. magnet 112 is to the right of magnet 106 FIG. 1). Further, outer magnet 112 has a magnetization vector 112c that points in a direction opposite of magnetization vector 110c or away from the plane in which lies top surfaces 102a, 104a,110a,112a of center-adjacent magnets 102, 104. That is to say, magnetization vector 112c is directed in the negative Y direction (−Y) as defined by the Cartesian coordinate system of FIG. 1 (i.e. magnetization vector 112c is pointed down in the example of FIG. 1 and thus is anti-parallel to magnetization vector 110c).

Thus, in the illustrative embodiment of FIG. 1 with the magnetization vector of magnets 102, 104, 106 directed in a minus Z direction (i.e. −Z as defined by the coordinate system of FIG. 1), the magnetization vector of outer magnet 110 is directed in the positive Y direction (+Y) and the magnetization vector of outer magnet 112 is directed in the negative Y direction (−Y) again, with all directions as defined by the Cartesian Coordinate system of FIG. 1. Accordingly, as explained above, in a Unilateral Linear Halbach configuration, the directions of the magnetization vectors of center, center-adjacent and outer magnets are provided having a particular relationship to each other.

With the above-described physical and magnetic structure, magnet array 100 is capable of generating a substantially uniform, directed magnetic field 108 in a working region above (i.e. in a positive Y direction from) recessed, center magnet 106. Further by appropriately selecting characteristics of the magnets or magnetic regions which produce magnet magnetic field 108, the magnetic field 108 may be provided having a strength sufficient to perform an NMR measurement oriented horizontal to the top surface of magnet array 100.

Thus, it may be said that the direction of the magnetization vectors of outer magnets 110, 112 are selected in concert with the direction of the magnetization vectors of magnets 102, 104, 106 (or alternatively, it may be said that the magnetization vectors of center and center-adjacent magnets 102, 104, 106 are selected in concert with the direction of the magnetization vectors of outer magnets 110, 112).

It should, however, be appreciated that in other embodiments, the magnetization vectors of magnets 102, 104, 106 may be directed in the +Z direction and in this case the magnetization vector of magnet 110 would be in the negative Y direction (−Y) and the magnetization vector of magnet 112 would be in the positive Y direction (+Y). With such an arrangement, a magnetic field 108 having a magnetization vector pointed in the −Z direction would be provided. Such a magnetic field would still be provided having a strength sufficient to perform nuclear magnetic resonance (NMR) oriented horizontal to the top surface of magnet array 100.

In the illustrative embodiment of FIG. 1, array of magnets 100 includes at least first, second, third, fourth, and fifth magnetization domains achieved through individual magnets (here five individual magnets) with three magnetization domains having like-pointed magnetization vectors and two magnetization domains having magnetization vectors which are antiparallel to each other and which are orthogonally directed with respect to the three like-pointed magnetization vectors.

As explained above, the magnetization domains are configured to provide a longitudinally directed magnetic field in a respective orientation or direction. The magnetization domains are disposed and orientated relative to one another as to produce a magnetic field with its flux concentrated on one surface (e.g. a top surface) of magnet array 100 with the field at an opposite surface (e.g. the bottom surface) of array of magnets 100 being effectively zero. In other words, the field at the opposing surface comprises regions having a magnetic field equal to zero and further regions having a non-zero magnetic field with high gradients (i.e. rapidly changing over space). As discussed in detail below, the flux concentrated on one end of array of magnets 100 provides substantially uniform field 108 (i.e. of a sufficient uniformity for performing an NMR measurement).

In the illustrative embodiment of FIG. 1, the first magnetization domain is provided by first magnet 102, the second domain is provided by second magnet 104, the third domain is provided by third magnet 106, the fourth domain is provided by fourth magnet 110, and the fifth domain is provided by fifth magnet 112.

Magnets 102-112 may comprise conducting coils, permanent magnets (e.g. neodymium iron boron, samarium cobalt, alnico, ceramic, ferrite, to name a few) or any combination thereof.

According to some embodiments, each magnet 102-112 may comprise one or more magnets of the same size. For example, magnets 102-112 may comprise cube-shaped magnets (cubic magnets) of the same size. In practical embodiments, cubic magnets having sides with lengths in the range of about 0.0625 to about 6 inches may be used. Magnets having lengths outside of these ranges are, of course, also possible, but may increase manufacturing and/or assembly complexities.

As noted above, magnets 102-112 each have top and bottom surfaces and at least one side surface and are effectively disposed equally spaced apart symmetrically with respect to a zero point of Y-axis 107. Magnet 106 is disposed so that a center point of magnet 106 is effectively in-line with a zero point of axis 109, in other words longitudinal axis 107 effectively symmetrically bisects magnet 106. Magnet 106 is orientated so that it produces a magnetic field in a direction substantially along a latitudinal axis 109 perpendicular to longitudinal axis 107. For example, in the illustrative embodiment of FIG. 1, magnet 106 has a magnetization vector 106c in a negative direction along axis 109.

Magnets 102 and 104 are disposed symmetrically on either side of magnet 106 (i.e. magnet 106 is disposed between magnets 102 and 104) along latitudinal axis 109 and have magnetization vectors 102c, 104c which are effectively parallel with respect to one another and axis 109. Magnets 102 and 104 are effectively equally spaced apart from magnet 106 in the Z direction (as defined by axis 109). Magnets 102 and 104 are further disposed so that the top surfaces 102a, 104a of magnets 102 and 104 lie in a plane parallel to axis 109. In the example of FIG. 1, surfaces 102a, 104a lie in the X-Z plane. Thus, the top surfaces of magnets 102 and 104 are at a same height.

The plane in which the top surfaces of magnets 102 and 104 lie is different from the plane in which lies the top surface of magnet 106. In other words, the top surface of magnet 106 is at a different height than that of the top surfaces of magnets 102 and 104. In the illustrative embodiment of FIG. 1, the top surface of magnet 106 is at a height depressed from (or recessed below) the height of the surfaces 102a, 104a of magnets 102 and 104.

Magnets 102 and 104 are oriented so that they each produce a magnetic field in the same direction as magnet 106. In this example, the direction is substantially along axis 109. For example, in the illustrative embodiment of FIG. 1, magnets 102 and 104 are oriented such that each produce a magnetic field having a magnetization vector in a negative direction substantially parallel to axis 109. Magnets 110 and 112 are disposed symmetrically around magnets 102 and 104 (i.e. magnets 102-106 are symmetrically disposed between magnets 110 and 112). Further, magnets 110 and 112 are effectively equally spaced apart from magnets 102 and 104, in the respective −/+Z directions (as defined by axis 109). Further still, outer magnets 110 and 112 are disposed so that the top surfaces 110a and 112a lie in the same plane in which lie the top surfaces of magnets 102 and 104 (i.e. the top surfaces 110a, 112a of magnets 110 and 112 are at the same height (or at substantially the same height so as to allow for NMR measurements) as the top surfaces 102a, 104a of magnets 102 and 104). In the example of FIG. 1, surfaces 110a, 112a lie in the X-Z plane. Thus, the top surfaces of center-adjacent and outer magnets 102 and 104, 110 and 112 are at the same height or substantially the same height.

It should be appreciated that magnets 110 and 112 are oriented such that they each produce magnetic fields substantially perpendicular to the magnetic field produced by magnets 102-106 (i.e. substantially parallel to longitudinal axis 107). The magnetic fields produced by magnets 110 and 112, however are anti-parallel in relation to each other.

For example, in the illustrative embodiment of FIG. 1, outer magnet 110 is oriented to provide a magnetization vector 110c directed in a positive direction along axis 107 and outer magnet 112 is oriented to produce a magnetization vector 112c directed in an opposite, negative direction along axis 107. Thus, the magnetic field vectors 110c, 112c, are said to be anti-parallel.

Because magnets 102-112 are disposed as described above, magnet array 100 produces magnetic field 108 having a flux concentrated at the top surfaces of magnets 102-112 and the field at the bottom surfaces of magnets 102-112 being inconsequential (e.g. effectively zero). At least a portion of the magnetic field concentrated at the top surfaces of magnets 102-112 comprises a substantially uniform magnetic field 108. Thus, as described above, a magnet or magnet array having a Unilateral Linear Halbach configuration produces a substantially uniform magnetic field 108 in a working region above a surface of magnets 102-112 and in this example, located above a surface of central magnet 106.

Ideally, magnetic field 108 has a substantially uniform magnetic strength over a predetermined area. In practical systems, magnetic field 108 has a substantially uniform magnetic strength over predetermined areas of sufficient uniformity to perform an NMR measurement. Those of ordinary skill in the art will appreciate that the sufficient uniformity needed to perform an NMR measurement is dependent upon the desired application as well as other aspects of the NMR sensor (e.g. radio frequency ("RF") coils and RF excitation pulse shapes). For example, a uniform magnetic field can be considered substantially uniform with a uniformity of ±8% for T2 relaxometry measurements, ±3% for measurements of diffusivity of a sample or a liquid within a sample to be measured, ±0.01% for measurements of chemical shifts, and ±20% for measurements of proton density or other measure of the number of spins within a sample to be measured.

The size and shape of the predetermined area is based upon the physical and magnetic characteristics and properties of the magnets which form magnet array 100 as well as the spacing of magnets 102-112, as in the case of an array of separate magnets as will be described in further detail below in conjunction with FIG. 2. Alternatively, in the case of a partially or fully integrated/unitary magnet (e.g. as shown FIGS. 1A, 1B, respectively) having separate magnetic domains (or regions), the size, shape and uniformity of the magnetic field 108 is based upon the physical and magnetic characteristics and properties of the magnetic regions in the integrated/unitary magnet portions.

According to some embodiments, the magnetic strength of substantially uniform magnetic field 108 may be in the range of 0.05 tesla to 0.5 Tesla, while in other embodiments the magnetic strength may be between 0.01 to 0.8 Tesla. Those of skill in the art will appreciate that the variance over the area of magnetic field 108 is dependent upon the application as well as other aspects of the NMR sensor, as discussed above.

Due to the uniformity of magnetic field 108, a large number of protons may be excited at substantially the same Larmor frequency thus enabling NMR to be performed.

As noted above, due to the configuration of magnets 102-112, magnetic field 108 is established above the plane in which magnet surfaces 102a, 104a, 110a, and 112a lie. In other words, array 100 produces a magnetic field 108 spaced a distance from a desired surface (here designated as "top" surface) of magnet array 100 in the Y direction. Further, magnetic field 108 is oriented so that it is directed substantially along axis 109 and, in a direction, opposite from the magnetization direction of magnets 102, 104, and 106. For example, in the illustrative embodiment of FIG. 1, magnetic field 108 is directed in a positive Z direction (i.e. +Z direction as defined by axis 109).

Figure 1A:
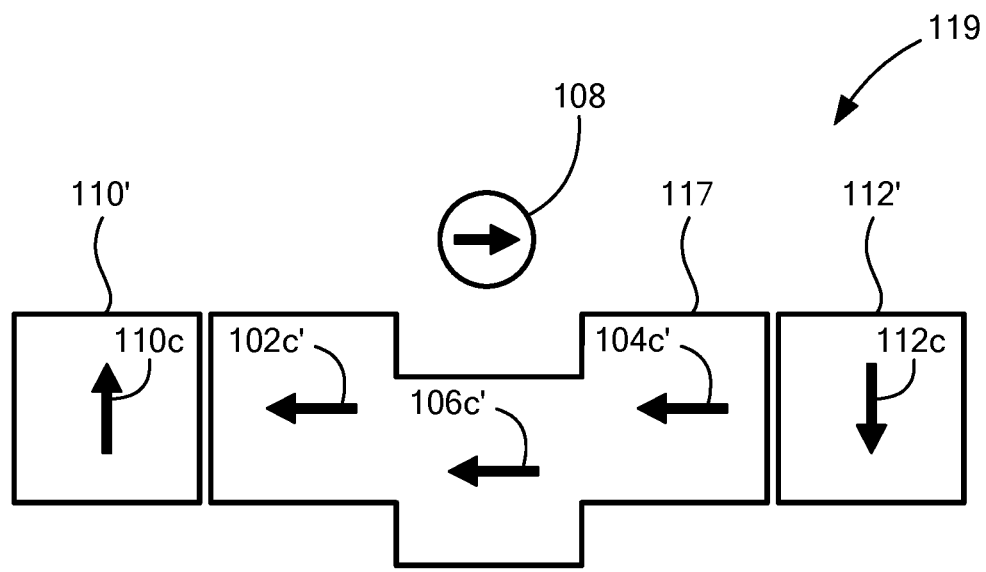
FIG. 1A is a block diagram of a Unilateral Linear Halbach magnet array with a partially integrated magnet.

Referring now to FIG. 1A, a Unilateral Linear Halbach configuration 119 includes a plurality of magnets, here three (3) physical magnets 117, 110', 112'. As noted above, in embodiments, the first, second, and third discrete magnetization domains (such as the domains provided by magnets 102, 104, and 106 in the illustrative embodiment of FIG. 1) may be provided from a single unitary, integrated magnetic material 117 (such as, for example a magnet having a generally U-shape) having three discrete magnetic domains disposed and orientated in the same directions as the magnetization vectors of respective ones of magnets 102, 104, and 106 as discussed above in conjunction with FIG. 1. In the illustrative embodiment of FIG. 1A, outer magnetization domains having magnetization vectors 110c, 112c are provided from separate magnets 110', 112' which may be the same as or similar to magnets 110, 112, described above in FIG. 1.

Figure 1B:
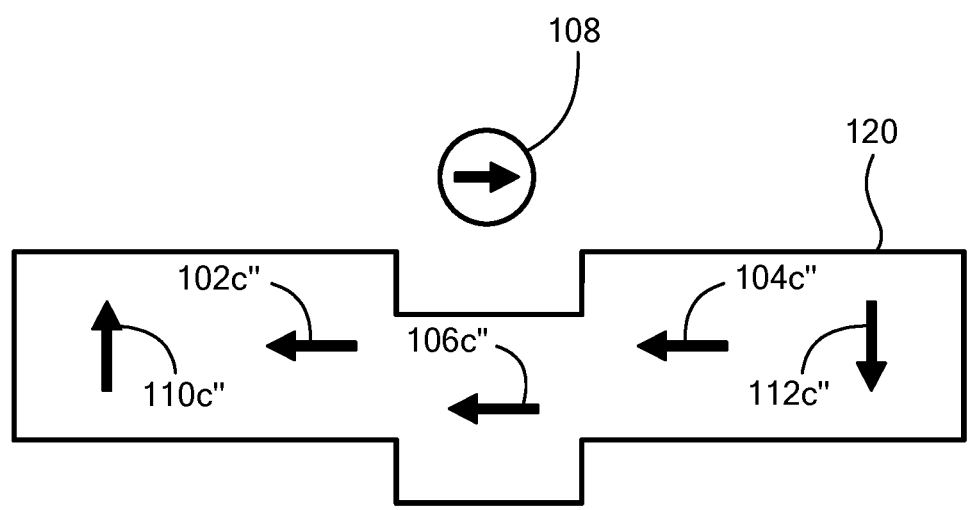
FIG. 1B is a block diagram of a Unilateral Linear Halbach magnet array with a fully integrated magnet.

Referring now to FIG. 1B, in other embodiments, the first, second, third, fourth, and fifth discrete magnetization domains may be provided by a single magnet 120 (i.e. a monolithic magnet) having five (5) discrete magnetization domains with magnetization vectors 102c'', 104c'', 106c'', 110c'' 112c'' oriented as shown and as described above in conjunction with magnets 102-112 of FIG. 1.

Figure 2:
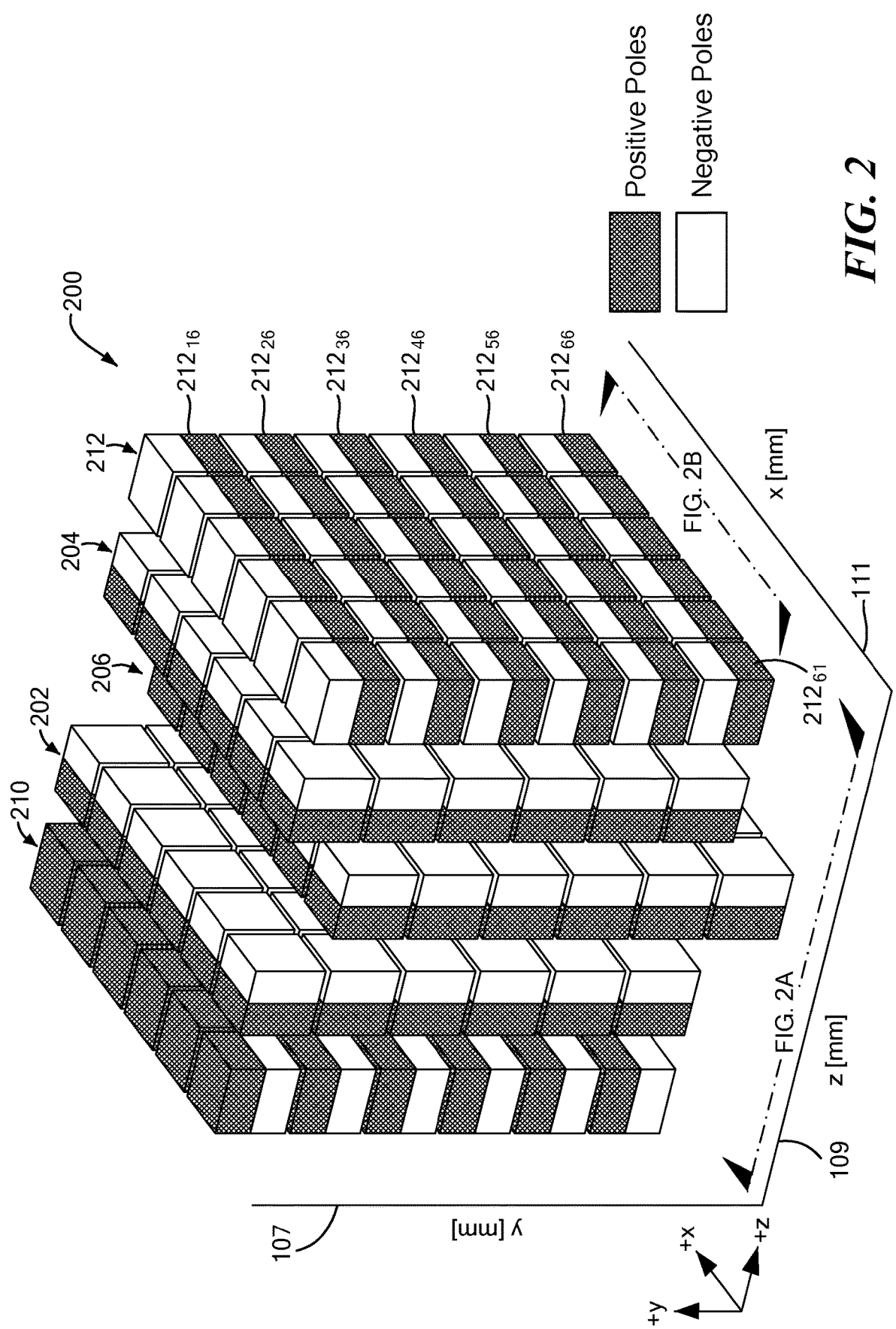
FIG. 2 is an isometric view of a magnet array arranged in a Unilateral Linear Halbach configuration.
Figure 2A:
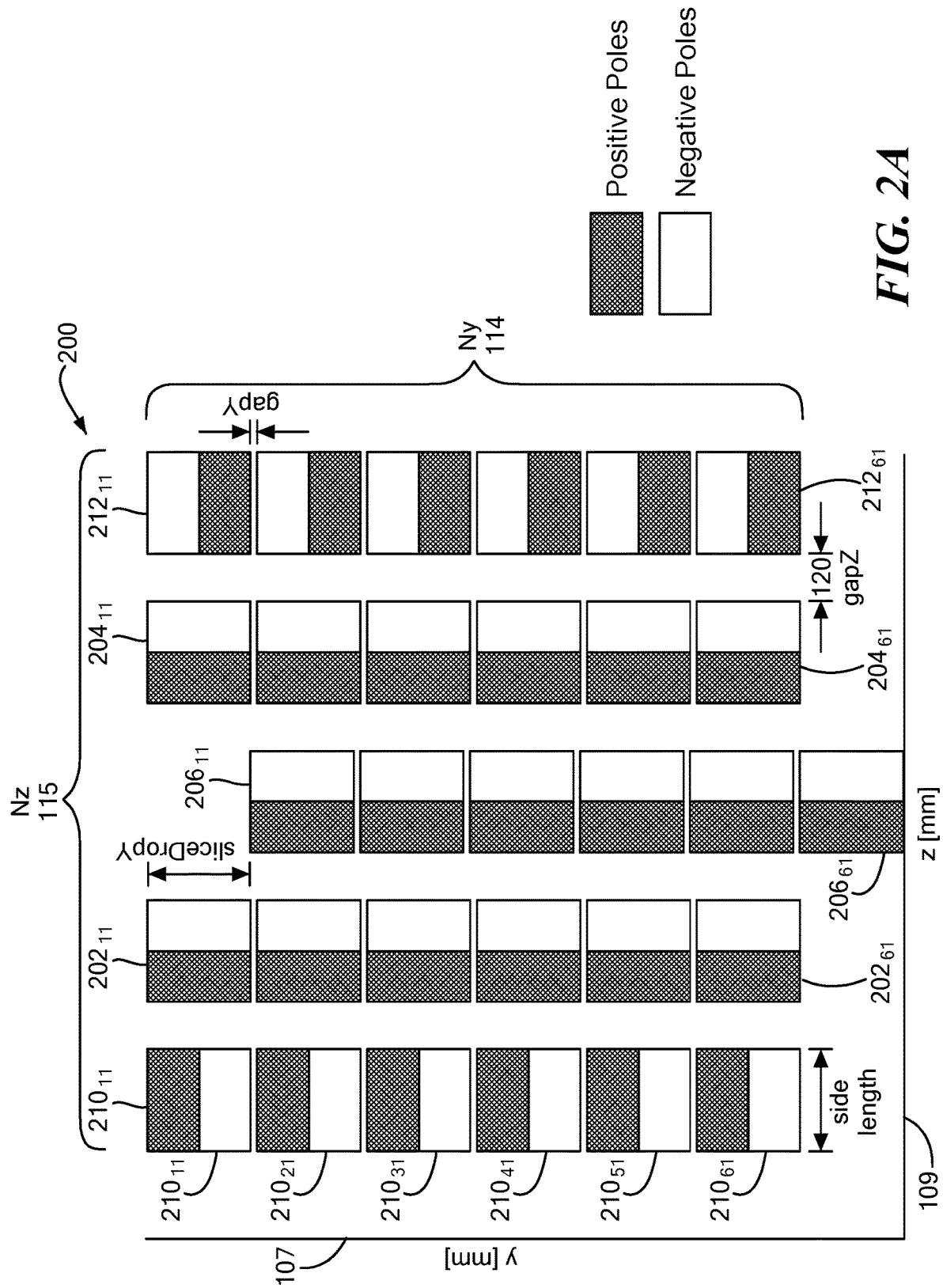
FIG. 2A is a side view of the Unilateral Linear Halbach magnet array of FIG. 2 in the YZ plane (according to the cartesian coordinates provided in FIG. 2)
Figure 2B:
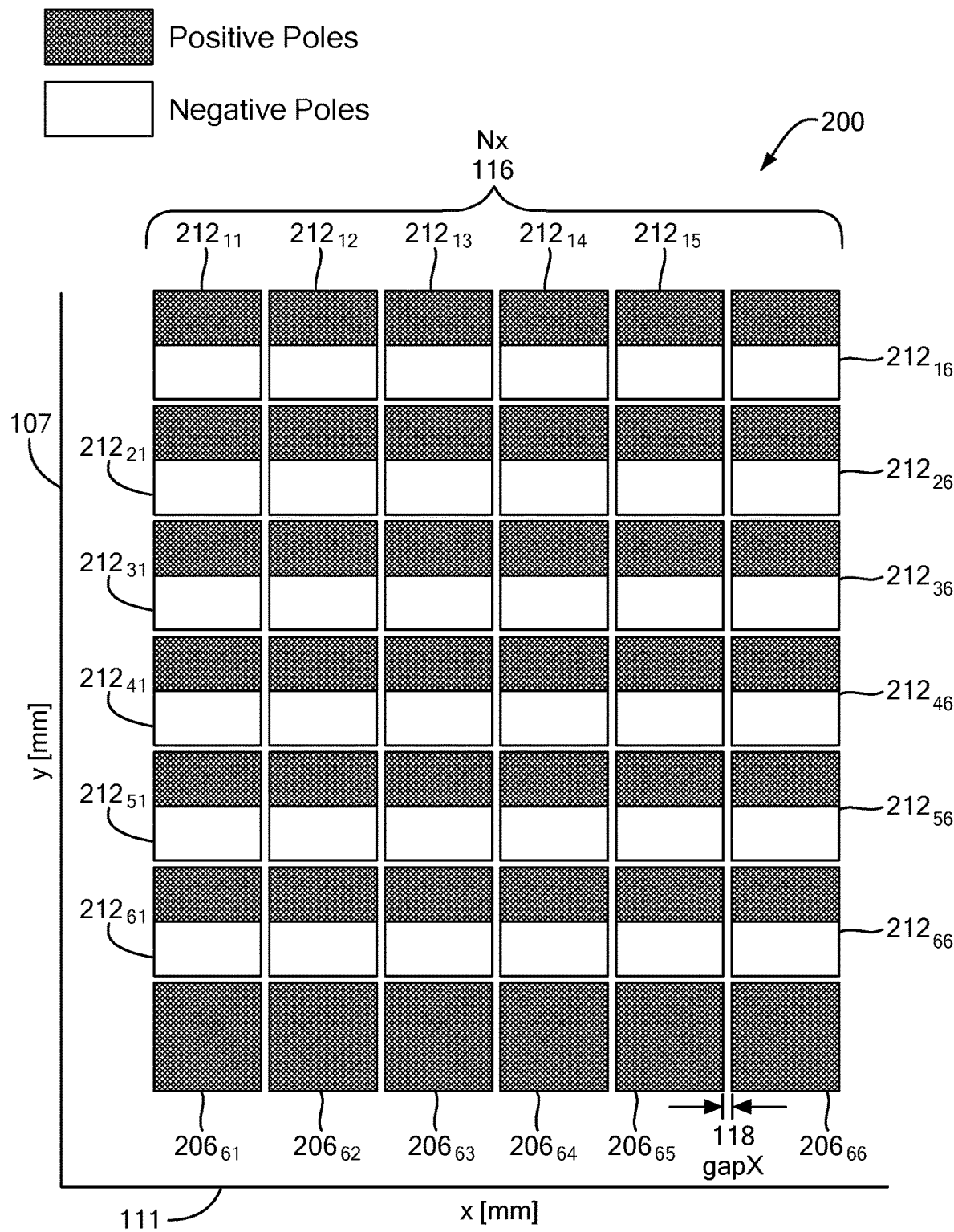
FIG. 2B is a side view of the Unilateral Linear Halbach magnet array of FIG. 2 in the XY plane.

Turning now to FIGS. 2-2B, in which like elements are provided having like reference designations throughout the several views, a Unilateral Linear Halbach magnet array 200 includes a plurality of magnet slices (or more simply "slices") 202-212. Each slice 202-212 comprises a plurality of magnets arranged in a planar array or matrix configuration. Each individual magnet may this be identified with subscripts representing a position within the matrix.

For example, taking slice 212 as representative of all slices 202-210, magnets in the first column of slice 212 are identified with sub-scripted reference numerals $212_{11}$-$212_{61}$ while magnets in the first row of slice 212 are identified with sub-scripted reference numerals $212_{11}$-$212_{16}$ with the subscripts corresponding to row, column position with the matrix. In embodiments, each slice 202-212 includes at least one magnet in a longitudinal direction (represented in in FIG. 2 as Y axis 207) and at least one magnet in a latitudinal direction (represented in FIG. 2 as Z axis 209).

In FIG. 2A, only one column from each slice 202-212 is visible. The number of rows in each slice 202-212 equals the number of magnets in the Y direction of the magnet array 200 and is denoted Ny (also identified with reference numeral 114 in FIG. 2A). The total distance spanned by magnets in the Y direction (which is referred to herein as a height of a slice) may thus be computed by summing both the length of each of the magnets in the Y direction and the spacing between magnets in the Y direction (with such spacing designated as gapY in FIG. 2A). In the illustrative embodiment of FIGS. 2-2B, the number of magnets in the Y direction for each slice is 6 (i.e. Ny=6 for magnet array 200).

Similarly, and referring still to FIG. 2A, the number of columns in magnet array 200 equals the number of magnets in the Z direction of the magnet array 200 and is denoted Nz (also identified with reference numeral 115 in FIG. 2A). The total distance spanned by magnets in the Z direction (which is referred to herein as a width of magnet array 200) may thus be computed by summing both the width of each of the magnets in the Z direction and the spacing between magnets in the Z direction (with such spacing designated as gapZ in FIG. 2A).

FIG. 2B presents a view of magnet array 200 with respect to the XY plane (as defined by the Cartesian coordinate system of FIG. 2). The number of columns in a slice 202-212 is equal to the number of magnets in the X direction and is denoted as Nx (and also with reference numeral 116) in FIG. 2B. In FIG. 2B, only one full slice 212 is visible with a single row $206_{61}$-$206_{66}$ of center recessed slice also being visible. Here, the number of magnets in the x direction is 6, therefore Nx is 6 for magnet array 200.

Each magnet of a matrix, or slice, may comprise magnets having one of a variety of different shapes including, but not limited to: a shape of a cube, a cube with rounded edges, a rectangular prism, a rectangular prism with rounded edges, an ellipsoid, or any combination thereof—to name a few. According to some embodiments, each magnet of a matrix, or slice, is of substantially the same size and shape (for example within manufacturing tolerances). In other embodiments, the magnets of a matrix are not each of substantially the same size allowing air gaps between some magnets of the matrix and no gaps between other magnets of the matrix.

In the illustrative embodiment of FIGS. 2A-B, each magnet of a matrix, or slice, may comprise a cube shaped magnet with a side length 122 (i.e. the length of each side of the cube).

Further, in the illustrative embodiment of FIGS. 2A-B, each magnet is effectively equally spaced apart from each adjacent magnet in the x direction by a first distance (also referred to herein as gapX) and from each adjacent magnet in the Y direction by a second distance (also referred to herein as gapY). In embodiments, the magnets in of each slice 202-212 are disposed so that the magnets along both the Y and X axes 107, 111 are effectively equally spaced apart. In embodiments, spacing gapX is not equal to spacing gapY. In embodiments, gapX spacing between each magnet is not equal. In embodiments, gapY spacing between each magnet is not equal.

In general, the uniformity and distances of gapX and gapY are selected to suit the needs of a particular application. For example, those of ordinary skill in the art will appreciate that varying the uniformity and distances of gapX and gapY may provide benefits by expanding the design space to allow higher performance at the cost of increasing the complexity of design and manufacturing necessary to achieve the desired uniformity and distances.

As can be seen most clearly in FIG. 2A, in the illustrative embodiment of FIGS. 2-2B, each magnet within a slice is effectively equally spaced apart from adjacent magnets in the Y direction by gapY 126. Further, as can be seen in the illustrative embodiment of FIG. 2B, each magnet within a matrix is effectively equally spaced apart from adjacent magnets in the X direction by a distance gapX 118. The area and magnetic strength of the substantially uniform field generated by array of magnets 200 is based, at least in part, upon the distances gapX 118, gapY 126, and gapZ 120, as discussed below with reference to FIG. 3.

Further, each matrix, or slice, 102-212 is disposed so as to be effectively parallel. According to some embodiments, each slice 102-212 is effectively parallel to one another within a margin of error of, for example, ±30%. Each slice is further effectively equally spaced apart from one another in the Z direction. In other words, a matrix 202-212 will have a distance of gapZ 120 between itself and adjacent matrices in the Z direction. According to some embodiments, each matrix will have a distance between 0 (i.e. each matrix is continuous along the Z axis) and three times the size of the matrix in the Z direction (i.e. the size of the sides of the magnets in the Z direction of the matrix) between itself and any adjacent matrices along the z axis (gapZ 120). In embodiments, gapZ 120 spacing between each magnet is not equal.

In general, the distance gapZ 120 is selected to suit the needs of a particular application. For example, those of ordinary skill in the art will appreciate that varying the uniformity and distance of gapZ 120 (as well as gapX 118 and gapY 126) may provide benefits by expanding the design space to allow higher performance at the cost of increasing the complexity of manufacturing and design necessary to achieve the desired uniformity and distances.

Each slice includes top and bottom surfaces and at least one side surface. The top surface of each slice corresponds to the top surfaces of each magnet at the positive most y direction of the slice. For example, in the illustrative embodiment of FIG. 2, the top surface of slice 210 comprises the top surfaces of the 8 magnets at 0 mm in the Y-direction (i.e. the positive most y direction within the matrix). Likewise, the bottom surface of each slice corresponds to the bottom surfaces of each magnet at the negative most Y-direction of the slice.

Each slice 202-212 provides a magnetic field oriented according to the orientation of each magnet within the slice. Each magnet within the slice is oriented such that the north pole of each magnet is oriented in the desired direction for the magnetic field of the slice 202-212 and the south pole of each magnet is oriented in the opposite of the desired direction. For example, slice 210 provides a desired magnetic field in a positive direction along the Y axis 107 (+Y). To provide the magnetic field in this direction, each magnet of slice 210 is oriented so that its north pole is in +Y direction and its south pole is in the −Y direction.

Slices 202-212 are arranged as a Unilateral Linear Halbach array, the configuration of which is discussed hereinabove with reference to FIG. 1. Meaning that the top surface of slices 202, 204, 210, and 212 lie in a plane and the top surface of slice 206 lies in a different plane. In this illustrative embodiment, the top surface of slice 206 lies in a plane which is below the plane in which the surfaces of slices 202, 204, 210, 212 lie and this slice 206 is said to be recessed with respect to slices 202, 204, 210, 212. The distance between these two planes in the Y direction (which corresponds to the displacement of the middle or center slice) is referred to herein as a "sliceDropY" distance.

Figure 2C:
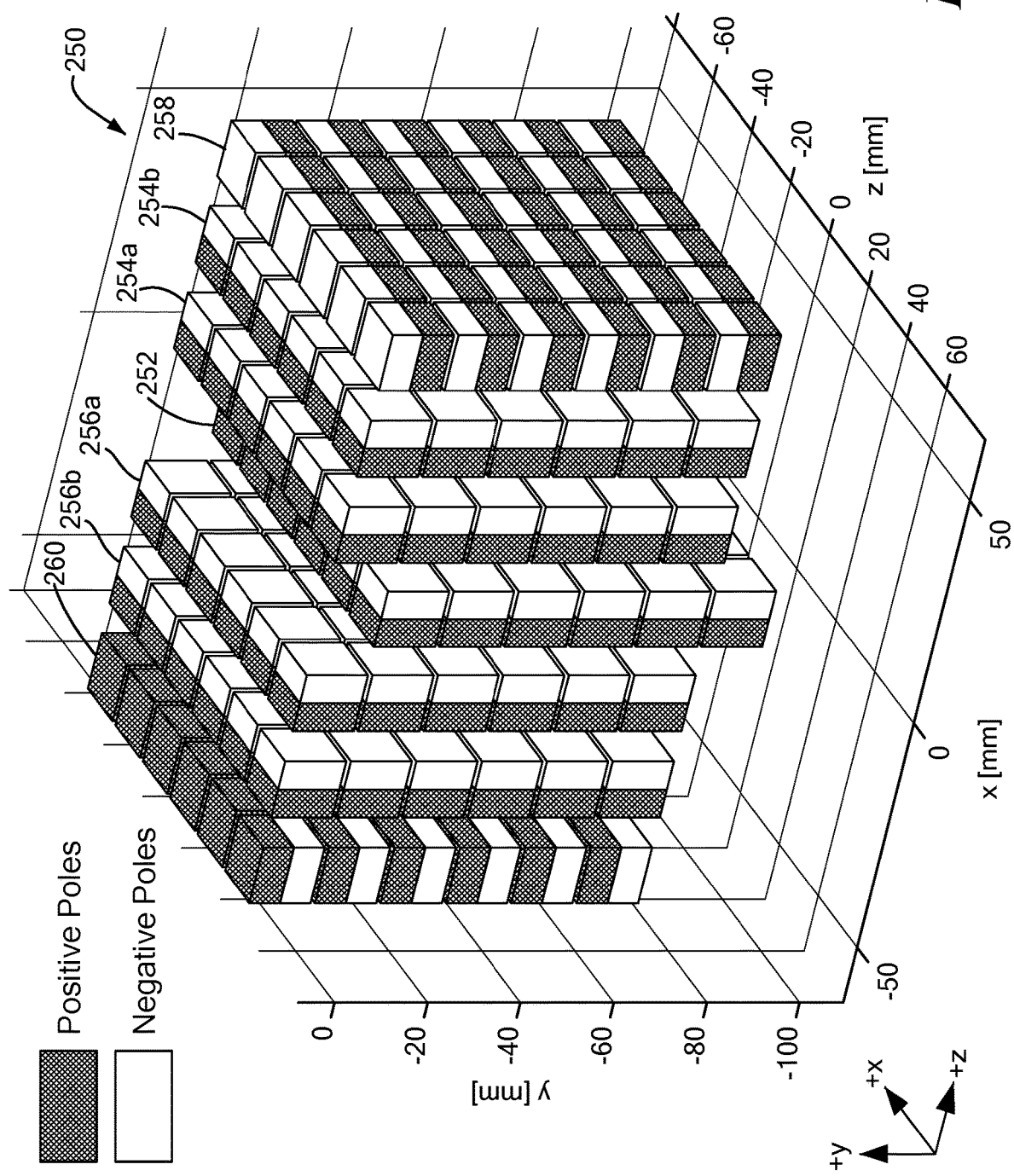
FIG. 2C is an isometric view of an embodiment of a Unilateral Linear Halbach magnet array having a plurality of center-adjacent magnet slices.

Referring now to FIG. 2C, an embodiment of a Unilateral Linear Halbach magnet array 250 includes a center slice 252, a plurality of center-adjacent slices 254a, 254b, 256a, 256b, and pair of outer slices 258, 260. In this illustrative embodiment, a pair of center-adjacent slices 254a, 254b, 256a, 256b are disposed on each side of the center slice 252. As described above, the magnetization vectors of each center-adjacent slice are in the same direction as each other as well in the same direction as the magnetization vector of the center slice. As also described above, the magnetization vector of the outer slices are anti-parallel and orthogonal to the direction of the magnetization vectors of the center and center-adjacent slices.

According to some embodiments, the orientation of center-adjacent slices (such as 254a, 254b, 256a, and 256b) may deviate from the orientation of the center slice (such as center slice 252). In embodiments, the orientation of a pair of center-adjacent slices may deviate (for example, by about ±20%) from the orientation of the center slice. It should be appreciated that these deviations may produce a higher performance magnet array at the cost of increasing the complexity of the manufacturing and design of the array. In embodiments, a pair of center-adjacent slices may not have a thickness (i.e. length in the Z direction) different from that of the center slice. In embodiments, the top surfaces of a pair of center-adjacent slices may not lie in the same plane as the top surfaces of the outer slices or in the same plane as each other. Likewise, in embodiments, it may be desirable or necessary that the top surfaces of the outer slices not lie it the same plane. For example, the top surfaces of the center-adjacent slices may be offset by −5 mm in the Y direction from the plane in which the top surfaces of the outer slices lie and the top surface of the central slice may be offset by −11 mm in the Y direction from the plane in which the top surfaces of the outer slices lie.

In embodiments, the top surfaces of each center-adjacent slice within a pair of center-adjacent slices may not lie in the same plane. In other words, each center-adjacent slice in a pair may not have the same Y direction displacement. For example, a first center-adjacent slice of a pair may have a top surface that lies in a first plane and a second center-adjacent slice of a pair may have a top surface that lies in a second plane. In embodiments, both the first plane and the second plane may be offset from the plane in which the top surfaces of the outer slices lie.

There exists a variety of reasons and factors why surfaces of slices may be adjusted up or down or rotated relative to each other such that the surfaces may or may not be in the same plane. For example, it may be desirable or necessary to direct (e.g. "tilt") a field in a working area to suit the needs of a particular application. It may be desirable or necessary to have a desired field depth or a desired field shape to suit the needs of a particular application. Also, since magnetic field characteristics of magnets may vary due to manufacturing tolerances (among other reasons), adjustments in the alignments of magnets may be necessary achieve a desired magnetic field in a desired working region. Other reasons may also exist for why it may be desirable or necessary for surfaces of slices (or magnets) may or may not be in the same plane.

Figure 2D:
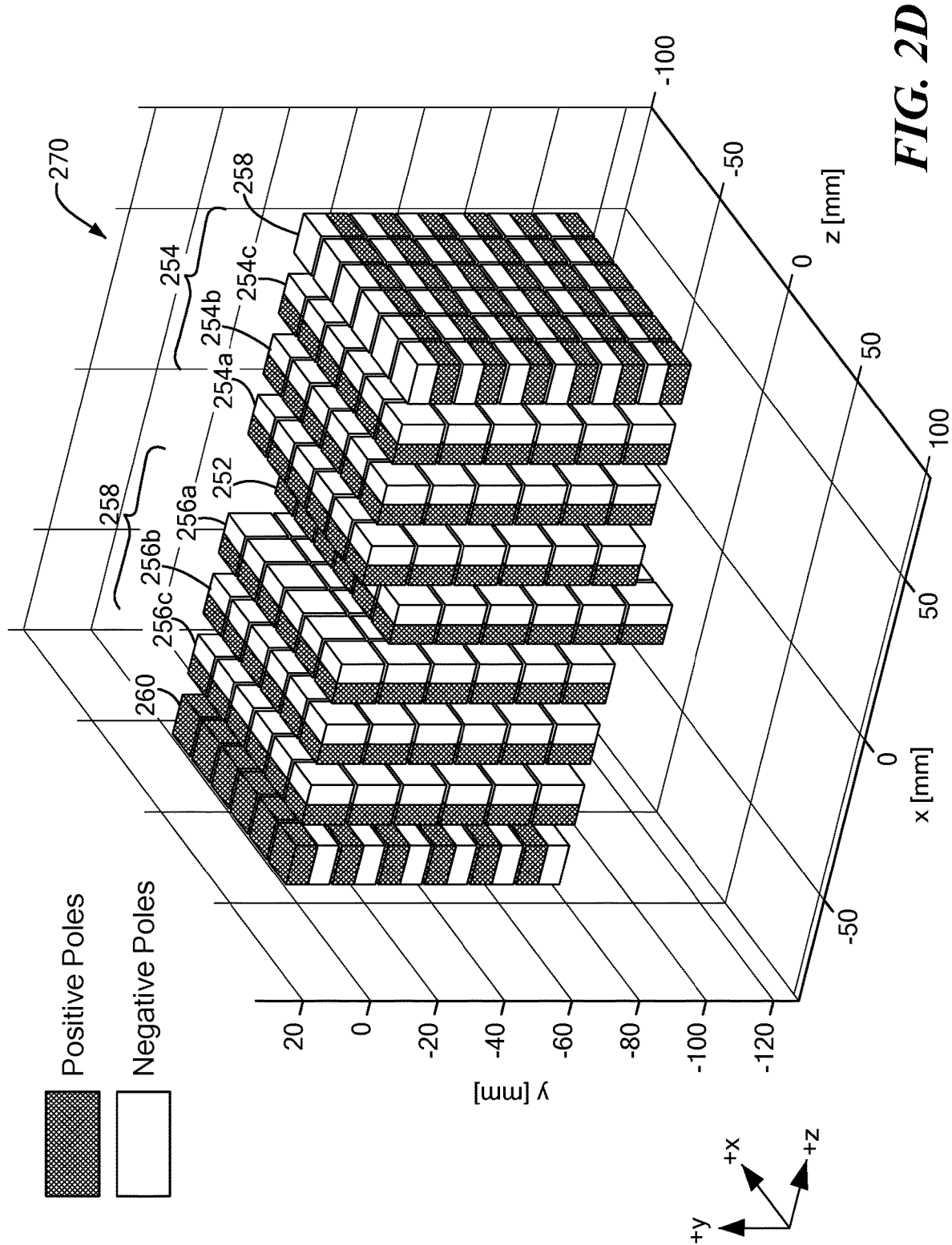
FIG. 2D is an isometric view of another embodiment of a Unilateral Linear Halbach magnet array having a plurality of center-adjacent magnet slices.

Referring now to FIG. 2D, in which like elements of FIG. 2C are provided having like reference designation, an embodiment of a Unilateral Linear Halbach magnet array 270 includes a center slice 252, a plurality of center-adjacent slices 254, 256 and pair of outer slices 258, 260. In this illustrative embodiment, a three center-adjacent slices 245a-254c and 256a-256c, are disposed on each side of center slice 252.

As described above, the magnetization vectors of each center-adjacent slice are in the same direction as each other as well in the same direction as the magnetization vector of the center slice. As also described above, the magnetization vectors of the respective outer slices are anti-parallel and orthogonal to the direction of the magnetization vectors of the center and center-adjacent slices. Further, as described above, a first outer slice is disposed away from the center slice in the same direction as the magnetization vector of the center slice and has a magnetization vector that points towards a plane in which the top surfaces of the center-adjacent slices lie Also, the second outer slice is disposed away from the center slice in a direction opposite of the magnetization vector of the center slice and has a magnetization vector that points away from the plane in which the top surfaces of the center-adjacent slices lie.

Figure 2E:
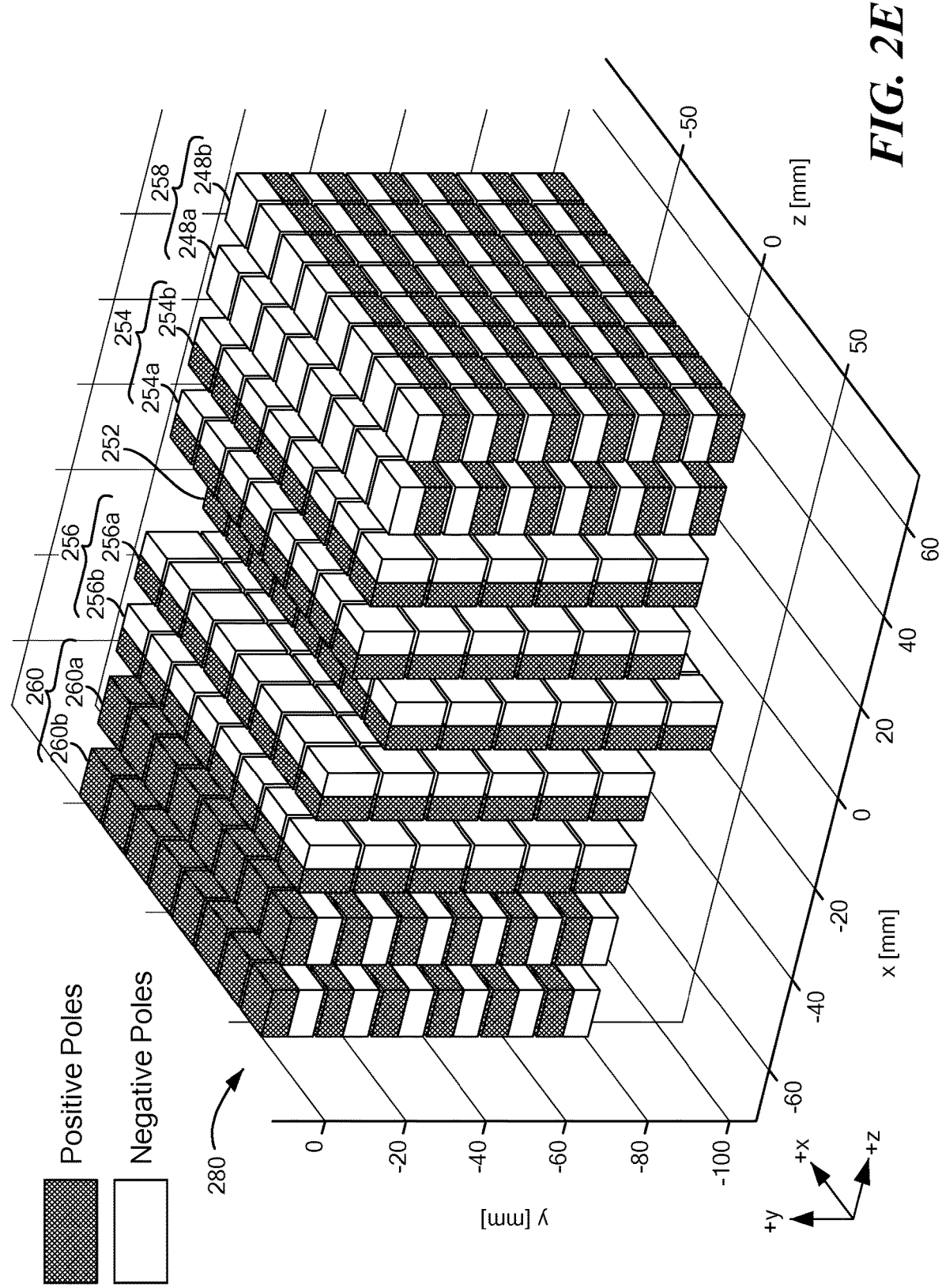
FIG. 2E is an isometric view of an embodiment of a Unilateral Linear Halbach magnet array having a plurality of center-adjacent magnet slices and a plurality of outer magnet slices.

Referring now to FIG. 2E, in which like elements of FIGS. 2C-2D are provided having like reference designation, an embodiment of a Unilateral Linear Halbach magnet array 280 includes a center slice 252, a plurality of center-adjacent slices 254, 256 and a plurality of outer slices 258a, 258b, 260a, 260b. In this illustrative embodiment, a pair of center-adjacent slices 254, 256 are disposed on each side of the center slice and a pair of outer slices 258, 260 are disposed adjacent the outer-most center-adjacent slices on each side of the magnet array. As described above, the magnetization vectors of each center-adjacent slice are in the same direction as each other as well in the same direction as the magnetization vector of the center slice.

Also, the magnetization vector of each pair of outer slices are in the same direction while the magnetization vector of opposing pairs of outer slices (i.e. pairs of outer slices disposed on the opposite, opposing side of the center slice) are anti-parallel. Further, the magnetization vectors of each pair of outer slices are orthogonal to the direction of the magnetization vectors of the center and center-adjacent slices.

Figure 2F:
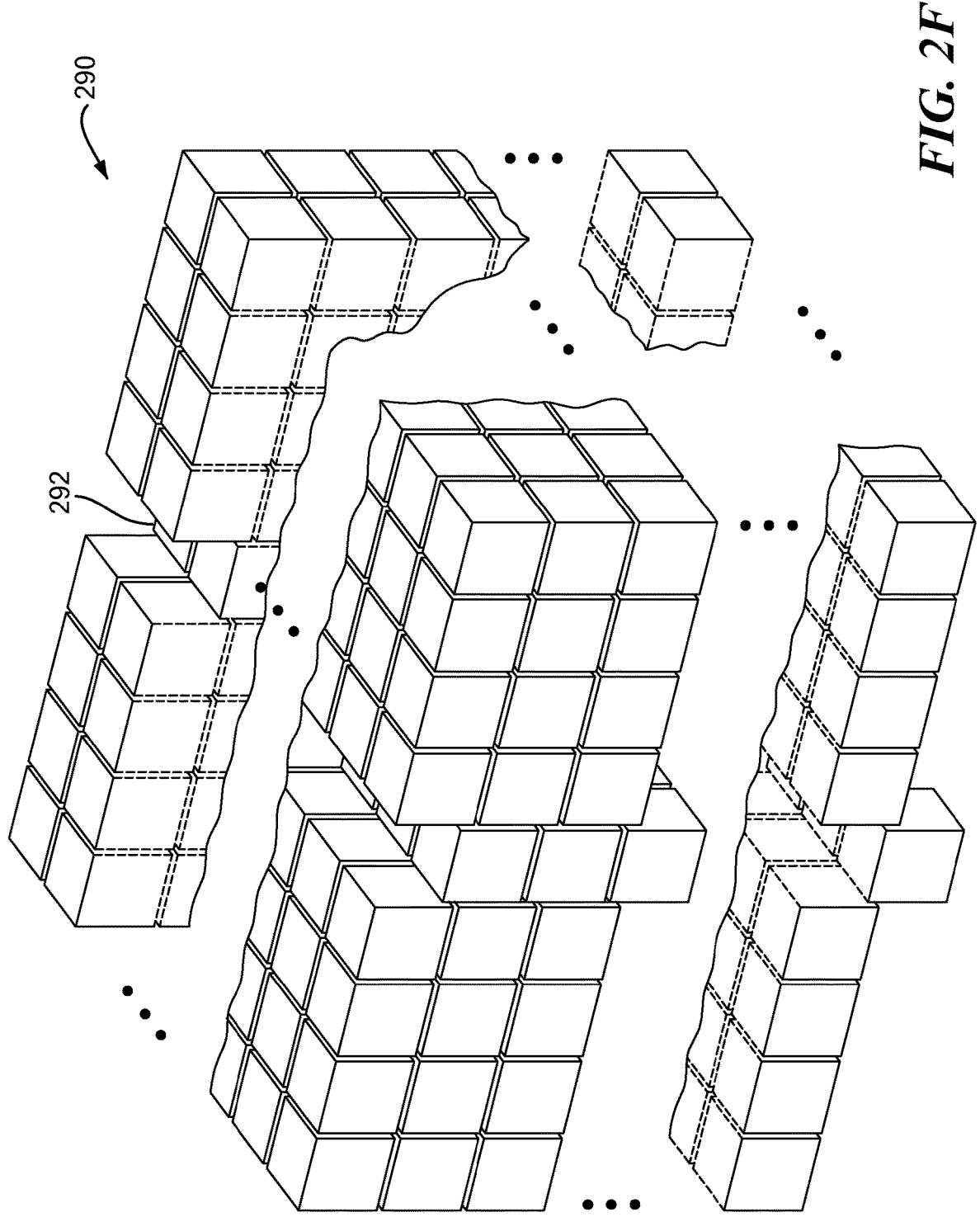
FIG. 2F is an isometric view of a generalized embodiment of a Unilateral Linear Halbach magnet array.

Referring now to FIG. 2F, a Unilateral Linear Halbach magnet array 290 includes a plurality of slices with each slice having a plurality of rows and columns. It should thus be appreciated that the number of slices as well as the number of rows and columns in each slice may be selected to suit the needs of a particular application. It should also be appreciated that although center slice 292 is shown as provided as a single slice, in embodiments, it may be desirable or even necessary to provide center slice 292 as a set of magnets comprising a plurality of slices. In embodiments, each top surface of a slice of a center slice may lie in different planes (i.e. may have different Y direction offsets).

Those of ordinary skill in the art, after reading the disclosure provided herein will understand how to select the number of slices as well as the number of rows and columns in each slice to use in a particular application. The factors to consider in making such selections includes, but is not limited to the size, shape, uniformity, position, field strength, and field direction of the magnetic field to be produced. It should also be appreciated that this process may include the use of commercially available tools to compute or simulate a field profile for a given configuration. In practice, the manner in which one of ordinary skill in the art may arrive at particular magnet design may include some combination of: 1) calculating magnetic field profiles by hand using analytical formulas; 2) calculating magnetic field profiles using analytical or numerical methods using software; 3) constructing, measuring, and iterating magnet arrays until a suitable design is found (i.e. an empirical approach). Other techniques may, of course, also be used.

Figure 3:
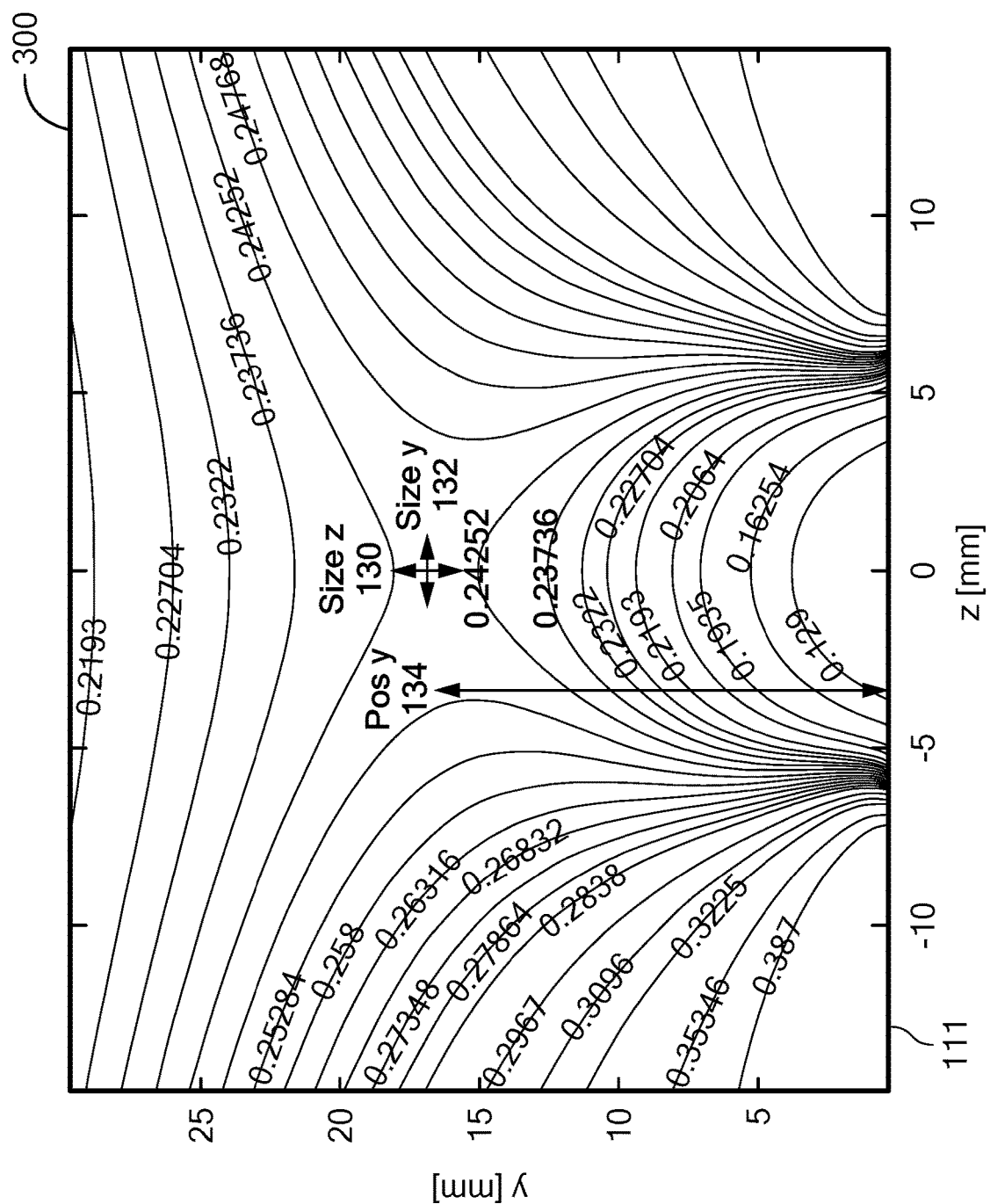
FIG. 3 is an example plot of magnetic field strength vs. position for a magnetic field generated by an array of magnets arranged in a Unilateral Linear Halbach configuration.

Referring now to FIG. 3, substantially uniform magnetic field 300 is generated by a Unilateral Linear Halbach magnet array such as magnet array 200 described above in conjunction with FIGS. 2-2B. Magnetic field 300 extends a height 134 (posY) above a surface of the magnet array (e.g. above top surface of magnet array 200 identified as the surface at y=0 in the illustrative embodiment of FIG. 2 and extending the in the positive Y direction). Magnetic field 300 is substantially centered about a center point of the magnet array (e.g. at the point (x0, z0) of magnet array 200 in FIGS. 2-2B). Magnetic field 300 has a substantially equal magnetic strength over a volume V, as measured from its center, is defined by a distance in the X direction (sizeX), a distance in the Y direction (sizeY 132), and a distance in the Z direction (sizeZ 130). Because volume V generally has a non-convex shape, its maximal extent in the x, y, and z directions may be greater than sizeZ, sizeY, and sizeZ respectfully.

According to some embodiments, sizeX, sizeY 132, and sizeZ 130 (and thus volume V) depend, at least in part, upon some, all or a combination of parameters: gapX 118, gapY 126, gapZ 120, Ny 114, Nz 115, Nx 116 and slicedropY 124.

According to some embodiments, metrics are derived from magnetic field 108 which define its geometry and strength to compare the fields generate by magnets with different configurations. Magnetic field 108 comprises a contiguous region $B_z(x,y,z)$ defined over a volume V, which maximizes an approximation of the signal to noise ratio (SNR) of a thermal noise limited NMR experiment:

$$SNR \cong \int_V B_Z(x,y,z)^{7/4} dV \quad [EQ. 2]$$

In some embodiments, the maximum field deviation within the uniform region, $B_z(V)$ is less than $\epsilon(1\%)$ which represents a reasonable bandwidth for a radio frequency (RF) excitation pulse:

$$\max(B_Z(V)) - \min(B_Z(V)) \le \epsilon * B_{Z,0} \quad [EQ. 3]$$

The maximum angular deviation of the magnetic field was constrained as off-axis precession can introduce artifacts into the measurement:

$$\tan^{-1}\sqrt{\frac{B_x(V)^2 + B_y(V)^2}{B_Z(V)^2}} \le 1°, \forall V \quad [EQ. 4]$$

The following metrics allow comparisons between magnet designs: field strength, size of uniform region, and its depth from the surface of the magnet. These metrics may be used to design a magnet array to suit the needs of a desired application.

FIGS. 4A-F, respectively, illustrate how varying gapX 118, gapY 126, gapZ 120, Ny 114, Nz 115, Nx 116 or slicedropY 124 affects sizeX, sizeY 132, and sizeZ. In the illustrative embodiments of FIGS. 4A-F, magnet array 200 (which generates magnetic field 300) has a magnet geometry with the values stated below in Table 1.

TABLE 1

| Magnet Geometry Parameter | Value |
|---|---|
| Magnet Side Length | 12.7 mm |
| Nx | 6 |
| gapX | 1 mm |
| Ny | 6 |
| gapY | 1 mm |
| Nz | 5 |
| gapZ | 6 mm |
| sliceDropy | 12 mm |

According to some embodiments, the magnetic field strength depth, and sizeX of magnetic field 300 is based upon Nx. As the number of slices in the x direction (Nx) increases the magnetic field strength and size in the x direction significantly increase while the depth of magnetic field 300 decreases. Varying Nx does not significantly change the shape of magnetic field 300, despite the changes in magnetic field strength and depth. According to an illustrative embodiment, Table 2, below, illustrates how magnetic field 300 changes as Nx is varied.

TABLE 2

| Nx | 5 | 6 | 7 | 8 |
|---|---|---|---|---|
| Magnetic field strength (Tesla) | 0.2141 | 0.2286 | 0.2429 | 0.2563 |
| Depth (mm) | 17.4 | 16.8 | 16.35 | 15.9 |
| sizeX (mm) | 14.4 | 14.4 | 15.0 | 16.2 |
| sizeY (mm) | 4.8 | 4.8 | 4.7 | 4.7 |
| sizeZ (mm) | 3.0 | 3.0 | 3.0 | 3.0 |

According to some embodiments, the magnetic field strength, depth, and sizeY of magnetic field 300 is based upon Ny. As the number of slices in the y direction (Ny) increases, the magnetic field strength increases and the depth decreases. Further, as Ny increases, sizeY decreases. Varying Ny does not significantly change the shape of magnetic field 300, despite changes in both magnetic field strength and depth. According to an illustrative embodiment, Table 3, below, illustrates how magnetic field 300 changes as Ny is varied.

TABLE 3

| Ny | 4 | 5 | 6 |
|---|---|---|---|
| Magnetic field strength (Tesla) | 0.217 | 0.240 | 0.256 |
| Depth (mm) | 17.7 | 16.5 | 15.9 |
| sizeX (mm) | 16.1 | 16.1 | 16.1 |
| sizeY (mm) | 4.9 | 4.8 | 4.7 |
| sizeZ (mm) | 3.0 | 3.0 | 3.0 |

Figure 4:
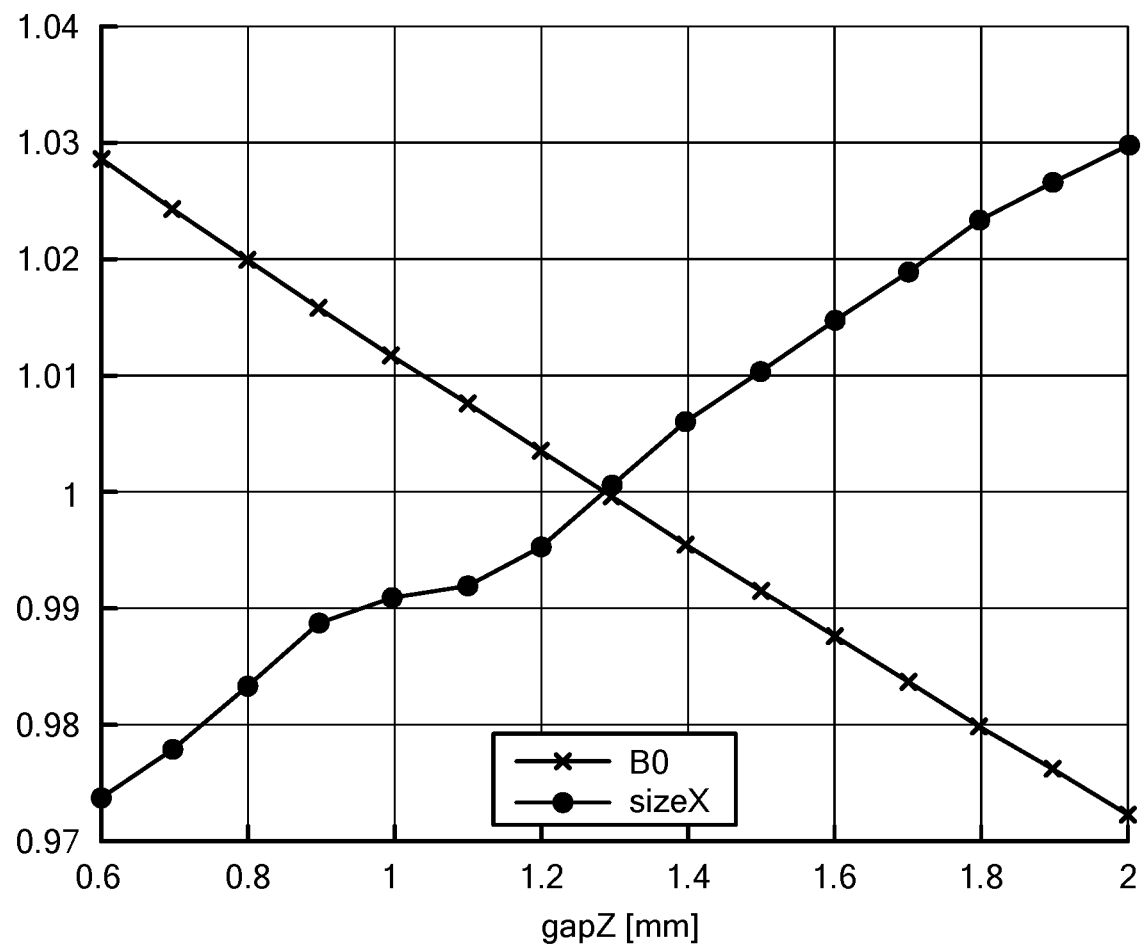
FIGS. 4-4E are plots which illustrate relative variation in magnetic performance metrics of a Unilateral Linear Halbach.
Figure 4A:
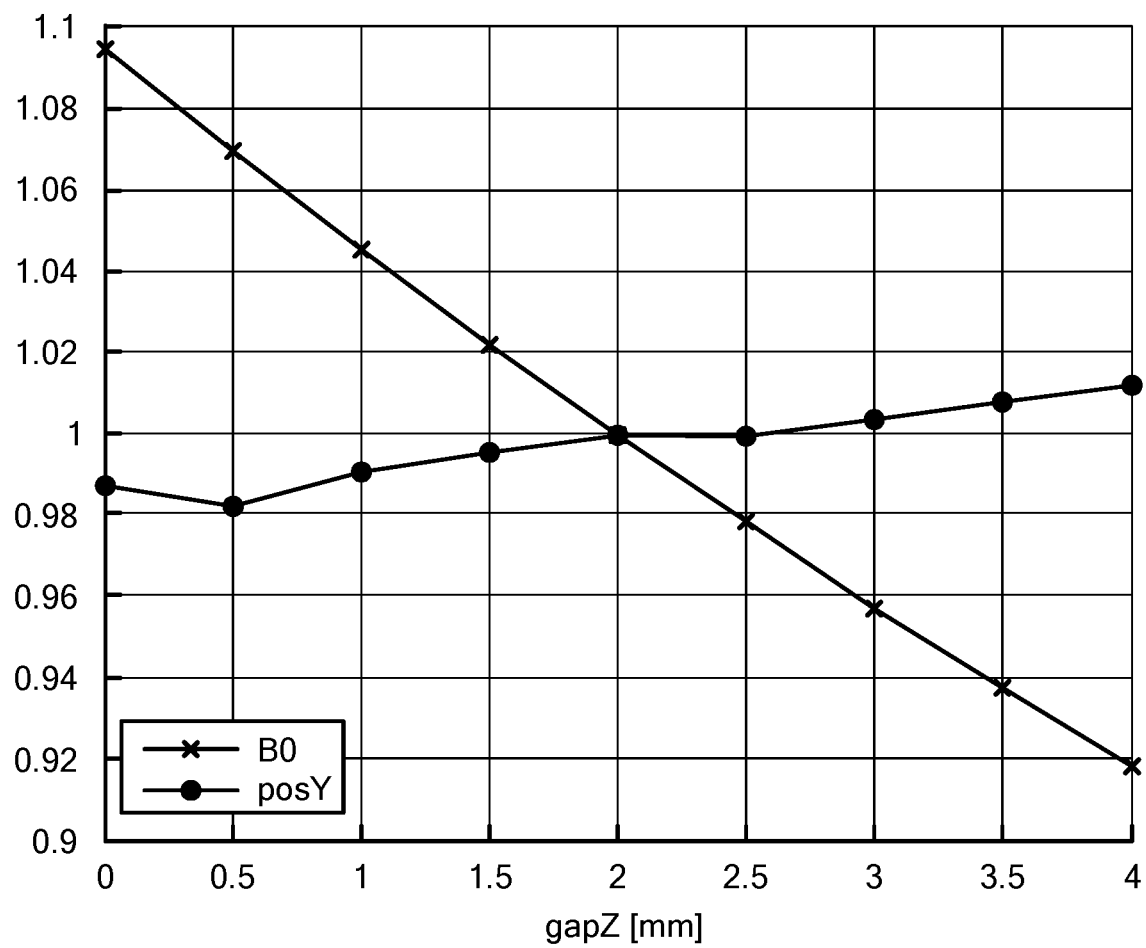

FIG. 4A represents changes in magnetic field 300 as gapX is varied. As gapX is increased, the magnetic field strength of magnetic field 300 is decreased and sizeX of magnetic field 300 is increased. According to an illustrative embodiment, Table 4, below, illustrates how magnetic field 300 changes as gapX is varied.

TABLE 4

| gapX | 0.6 mm | 1.3 mm | 2.0 mm |
|---|---|---|---|
| Magnetic field strength (Tesla) | 0.259 | 0.252 | 0.245 |
| Depth (mm) | 16.4 | 16.4 | 16.2 |
| sizeX (mm) | 16.8 | 17.1 | 17.4 |
| sizeY (mm) | 4.8 | 4.8 | 4.7 |
| sizeZ (mm) | 3.0 | 3.0 | 3.0 |

Figure 4B:
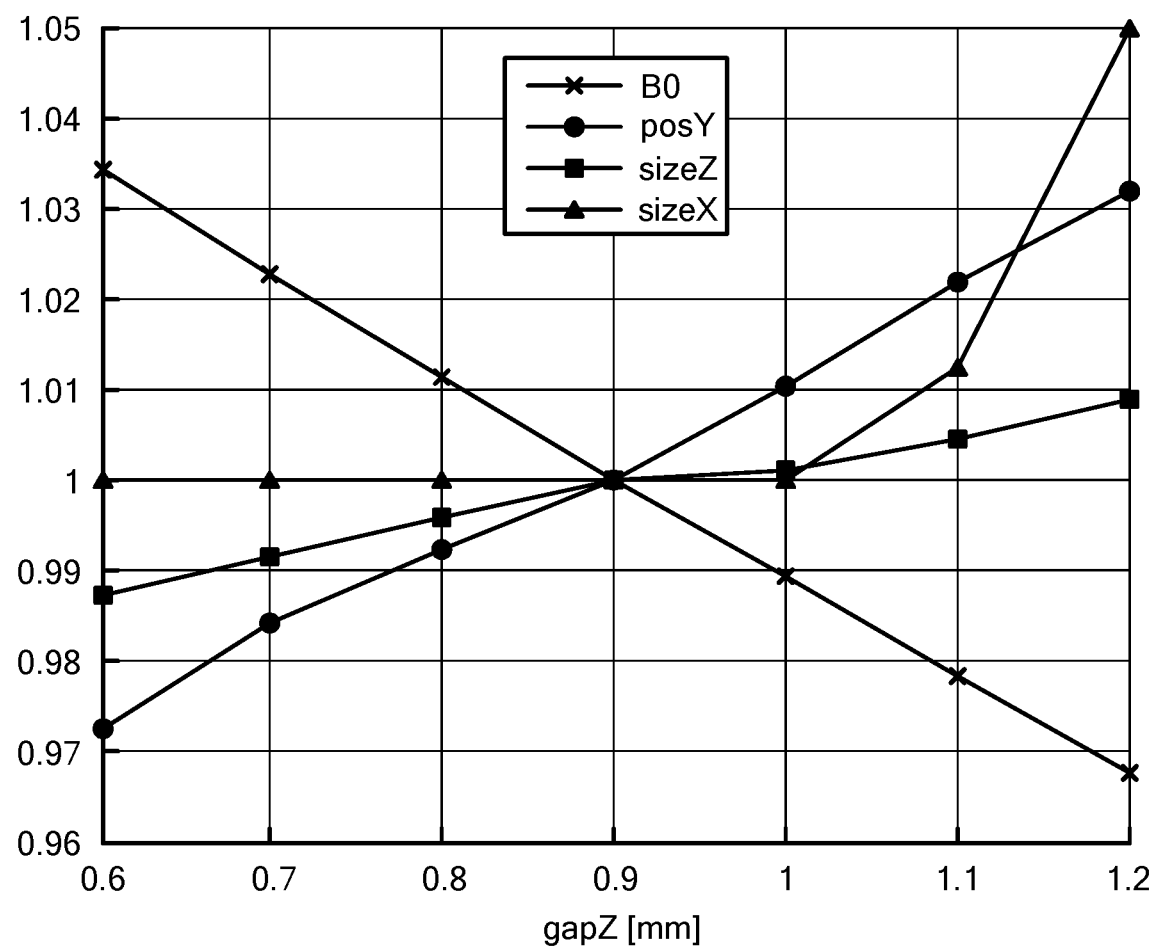

FIG. 4B represents changes in magnetic field 300 as gapY is varied. As gapY is increased, the magnetic field strength of magnetic field 300 is decreased and the depth of magnetic field 300 is increased. According to an illustrative embodiment, Table 5, below, illustrates how magnetic field 300 changes as gapY is varied.

TABLE 5

| gapY | 0.0 mm | 2 mm | 4 mm |
|---|---|---|---|
| Magnetic field strength (Tesla) | 0.262 | 0.240 | 0.220 |
| Depth (mm) | 16.4 | 16.6 | 16.8 |
| sizeX (mm) | 16.8 | 17.1 | 17.1 |
| sizeY (mm) | 4.8 | 4.8 | 4.7 |
| sizeZ (mm) | 3.0 | 3.0 | 3.0 |

Figure 4C:
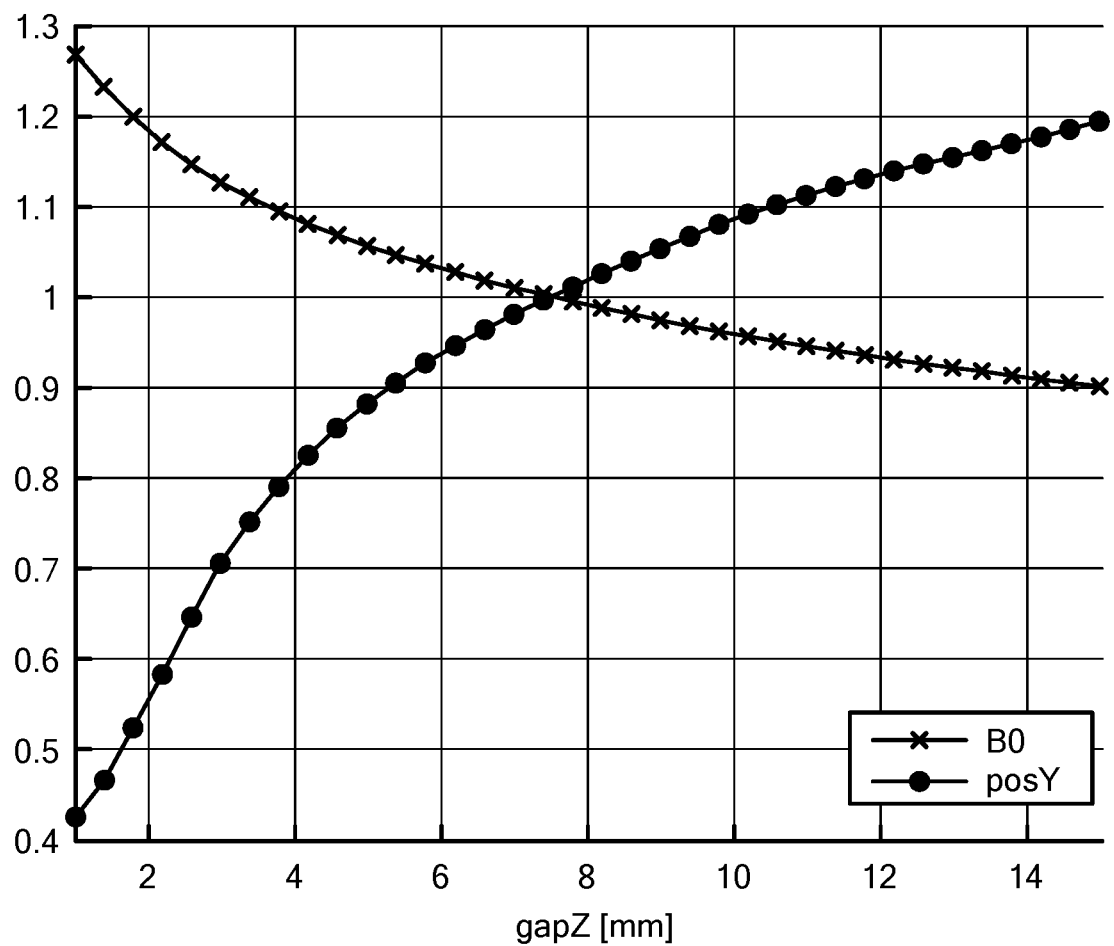

FIG. 4C represents changes in magnetic field 300 as gapZ is varied. As gapZ is increased, the magnetic field strength of magnetic field 300 is decreased while the depth, sizeX, and sizeY of magnetic field 300 are increased. According to an illustrative embodiment, Table 6, below, illustrates how magnetic field 300 changes as gapZ is varied.

TABLE 6

| gapZ | 0.6 mm | 0.9 mm | 1.2 mm |
|---|---|---|---|
| Magnetic field strength (Tesla) | 0.270 | 0.261 | 0.253 |
| Depth (mm) | 15.8 | 16.3 | 16.8 |
| sizeX (mm) | 16.4 | 16.7 | 16.8 |
| sizeY (mm) | 4.6 | 4.7 | 4.9 |
| sizeZ (mm) | 3.0 | 3.0 | 3.0 |

Figure 4D:
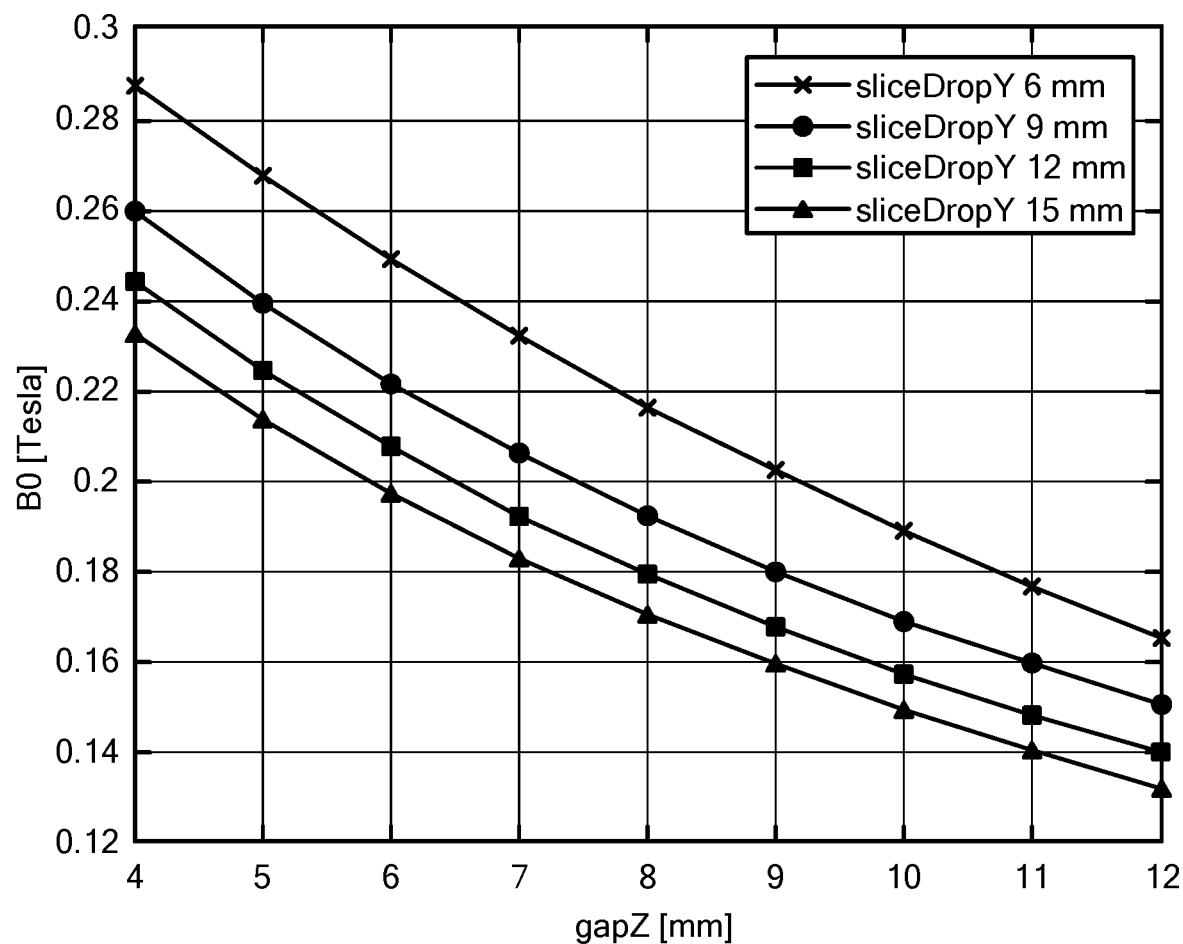

FIG. 4D represents changes in magnetic field 300 as sliceDropY is varied. When sliceDropY is below 1 mm, no substantially uniform region is generated above array of magnets 200. As sliceDropY becomes greater than 1 mm, the depth of the uniform region increases with a more isotropic shape and the magnetic field strength of magnetic field 300 decreased. The rate of decrease in the magnetic field strength and the rate of increase in the depth of magnetic field 300 both decreased as sliceDropY increased. According to an illustrative embodiment, Table 7, below, illustrates how magnetic field 300 changes as sliceDropY is varied.

TABLE 7

| sliceDropY | 1 mm | 8 mm | 15 mm |
|---|---|---|---|
| Magnetic field strength (Tesla) | 0.3467 | 0.271 | 0.246 |
| Depth (mm) | 6.3 | 15.2 | 17.7 |
| sizeX (mm) | 13.5 | 16.5 | 16.8 |
| sizeY (mm) | 1.2 | 4.7 | 4.8 |
| sizeZ (mm) | 6.9 | 3.0 | 3.0 |

Figure 4E:
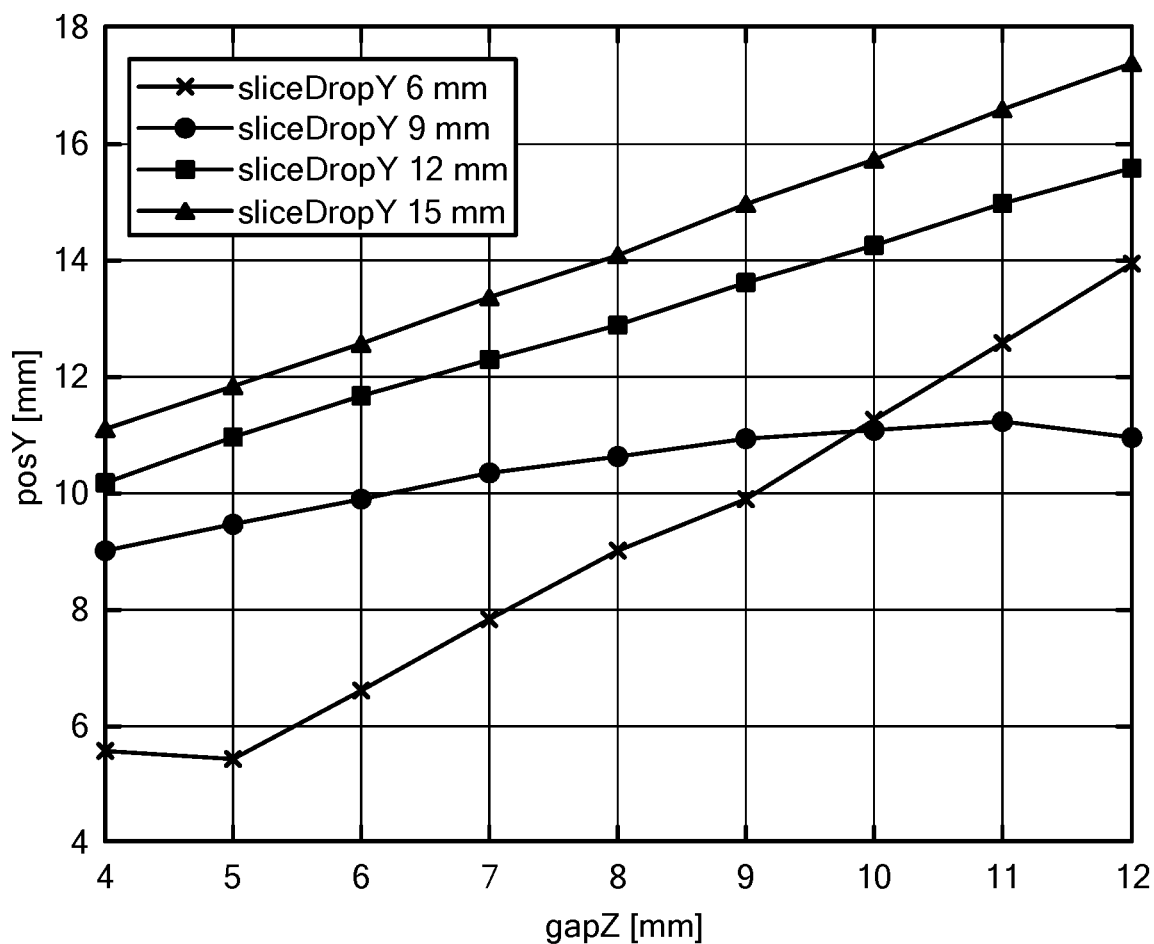

FIG. 4E represents changes in magnetic field 300 as both gapZ and sliceDropY are varied. In addition to changes in magnetic field 300 when gapZ and sliceDropY are varied as discussed above with reference to FIGS. 4C and D, magnetic field 300 is only produced by array of magnets 200 when the ratio of gapZ to sliceDropY remains within a desired range. When either sliceDropY was very small or gapZ was very large, magnetic field 300 is not well defined directly above the middle of array of magnets 200.

Figure 5:
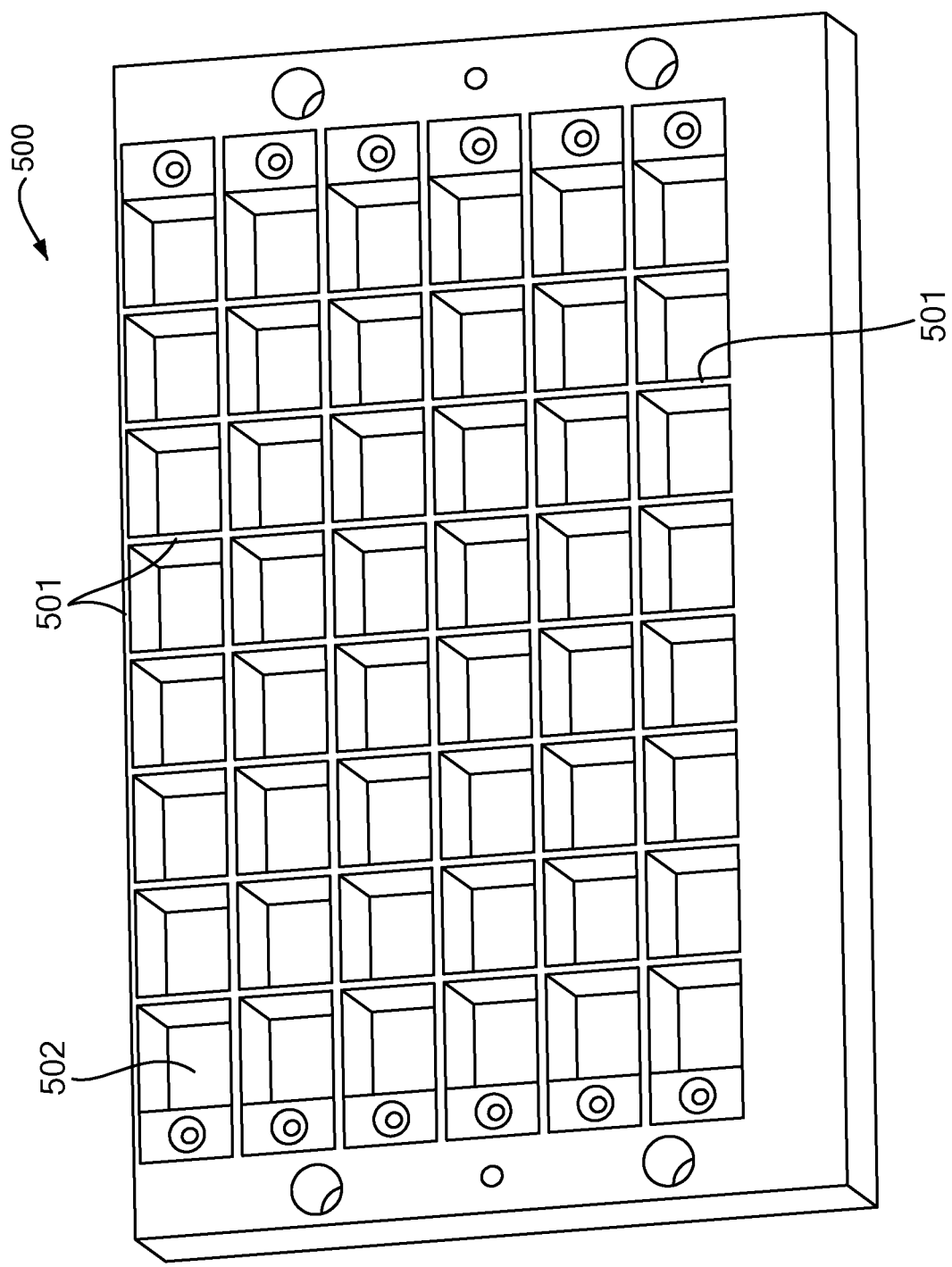
FIG. 5 is an isometric view of a housing capable of holding an array (or slice) of magnets.
Figure 5A:
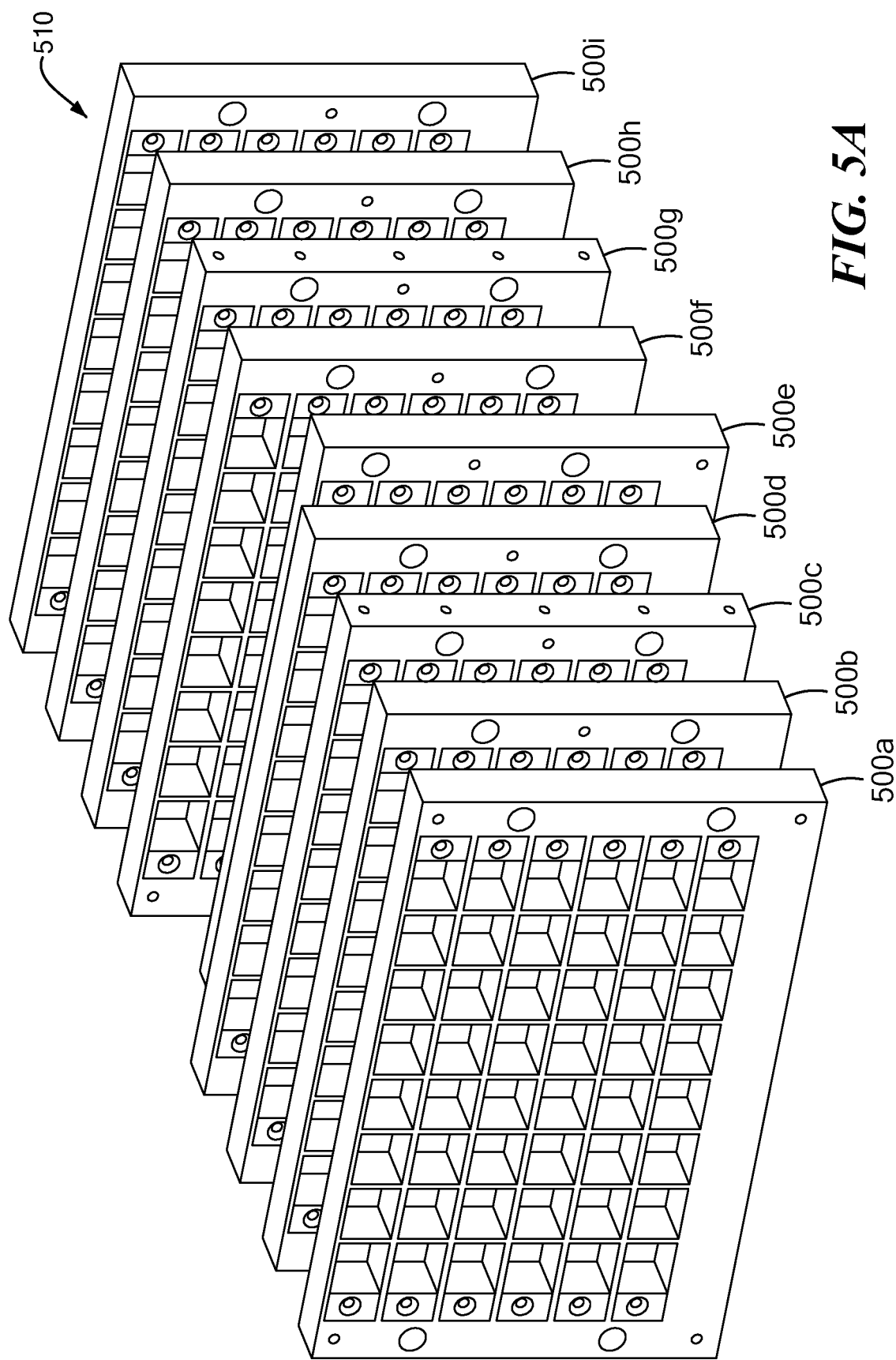
FIG. 5A is an isometric view of a plurality of housings arrange to provide a magnet array having nine (9) slices which may be the same as or similar to the magnet array described in conjunction with FIG. 2D.

Turning now to FIGS. 5 and 5A in which like elements are provided having like reference designations, a housing 500 is provided having a plurality of walls 501 which define openings 502 and provide housing 500 having a shape corresponding to a shape of a desired magnet array. Each opening 502 has dimensions selected to accommodate an individual magnet (e.g. any of the magnets described above in conjunction with FIGS. 1-4E). Because some magnets (e.g. neodymium) are in a highly unstable, high energy state when placed into the desired configuration of a Unilateral Linear Halbach array, a housing or other mechanical structure capable of restraining the individual magnets may be necessary.

According to some embodiments, housing 500 may be comprised of a heat treated, high strength, nonmagnetic alloy (e.g. 6061 aluminum or 7075 aluminum). This allows the housing to be of high strength and low magnetic susceptibility while also exhibiting good electrical and thermal conductivity. Electrical conductivity is important to reduce noise of the system by allowing it to act as a ground plane. Thermal conductivity is important because it allows the temperature regulation system to control the temperature of the magnets more quickly and effectively than otherwise would be the case.

In embodiments, housing 500 may include a temperature regulation system to provide temperature control. Such a temperature regulation system may comprise fluid paths integrated into or around portions of housing 500 that surrounds magnets disposed therein. By circulating a fluid (e.g. a liquid such as water or other liquid) at a desired temperature, housing 500 and subsequently magnets disposed in the housing will equilibrate at the same temperature as the water or other circulating liquid through conductive heat transfer. The fluid within the fluid paths may be supplied by a water bath, ice bath, circulating pump, fluid reservoir, or any combination thereof.

Housing 500 is configured to constrain the position and orientation of each of the individual magnets that comprise array of magnets (e.g. one of the slices in magnet array 270 in FIG. 2D). Further, housing 500 is configured such that each magnet can be easily and safely inserted without experiencing intractable forces from adjacent magnets. According to some embodiments, to avoid undue cost, housing 500 may be designed to be milled using standard computer numerical control ("CNC") milling techniques.

Referring now to FIG. 5A a series of housings 500a-500i (each of which may be the same or similar to housing 500 of FIG. 5) are configured to be coupled so as to form an array of magnets having a configuration which may be the same as or similar to magnet array 270 in FIG. 2D. It should be noted that housing 500e is offset (such as in the Y direction) relative to housings 500a-500d and 500f-500i.

Having described preferred embodiments which serve to illustrate various concepts, structures and techniques which are the subject of this patent, it will now become apparent to those of ordinary skill in the art that other embodiments incorporating these concepts, structures and techniques may be used. Accordingly, it is submitted that that scope of the patent should not be limited to the described embodiments but rather should be limited only by the spirit and scope of the following claims.

All publications and references cited herein are expressly incorporated herein by reference in their entirety.

What is claimed is:

1. A magnet assembly, comprising:
a pair of spaced apart first magnets having both magnetization poles oriented in a same direction and having at least one surface substantially aligned in a single plane; and
at least one second magnet disposed in the space between the first magnets, the at least one second magnet having a surface offset from the single plane and being arranged symmetrically with respect to a central longitudinal axis of the magnet assembly, said pair of spaced apart first magnets and each of said at least one second magnet having magnetization vectors directed in the same direction;
a first outer magnet disposed adjacent a first one of the pair of spaced apart first magnets, said first outer magnet having at least one surface substantially aligned in a single plane with like surfaces of the pair of spaced apart first magnets and said first outer magnet having a magnetization vector directed in a direction which is orthogonal to a direction of the magnetization vectors of the pair of spaced apart first magnets;
a second outer magnet disposed adjacent a second one of the pair of spaced apart first magnets, said second outer magnet having at least one surface substantially aligned in the single plane with like surfaces of the pair of spaced apart first magnets and said second outer magnet having a magnetization vector directed in a direction which is orthogonal to the direction of the magnetization vectors of the pair of spaced apart first magnets and which is in a direction which is opposite the direction of the magnetization vector of said first outer magnet;
whereby the first and second magnets and first and second outer magnets generate a substantially uniform magnetic field of sufficient strength to perform a nuclear magnetic resonance (NMR) process in a working region above at least one of the first and second magnets.

2. The magnet assembly of claim 1, wherein the first outer magnet is further disposed away from the central longitudinal axis in the direction of the magnetization vectors of the pair of spaced apart first magnets.

3. The magnet assembly of claim 2, wherein the first outer magnet has a magnetization vector directed towards the single plane.

4. The magnet assembly of claim 1, wherein the uniform magnetic field is located above a central region of the first and second magnets.

5. The magnet assembly of claim 1, wherein the first magnets, second magnets, first outer magnets and second outer magnets are disposed in a housing.

6. A magnet assembly, comprising:
a first center-adjacent magnet having a magnetization poles oriented in a first direction and having a first surface;
a second center-adjacent magnet spaced apart from said first magnet, said second magnet having a magnetization pole oriented in the first direction and having a first surface;
at least one center magnet disposed in the space between the first and second center-adjacent magnets, said center magnet having a magnetization pole oriented in the first direction and having a first surface offset from the first surfaces of the first and second center-adjacent magnets and being arranged symmetrically with respect to a central longitudinal axis of the magnet assembly;
a first outer magnet having a first surface, said first outer magnet disposed away from the central longitudinal axis in the direction of the magnetization vectors of the first and second center-adjacent magnets and proximate the first center-adjacent magnet, said first outer magnet having a magnetization vector directed in a direction which is orthogonal to a direction of the magnetization vectors of the first center-adjacent magnet and pointed in the direction of the first surface of the first center-adjacent magnet;
a second outer magnet having a first surface, said second outer magnet disposed proximate the second center-adjacent magnet, said second outer magnet having a magnetization vector directed in a direction which is orthogonal to the direction of the magnetization vectors of the second center-adjacent magnet and which is in a direction which is opposite the direction of the magnetization vector of said first outer magnet;
whereby the first and second center-adjacent magnets and first and second outer magnets generate a substantially uniform magnetic field of sufficient strength to perform a nuclear magnetic resonance (NMR) process in a working region above the first surfaces of the first center-adjacent, second center-adjacent and center magnets.

7. The magnet assembly of claim 6, wherein the first surfaces of the first and second center-adjacent magnets are substantially aligned a single plane.

8. The magnet assembly of claim 6, wherein the first surfaces of the first and second outer magnets are substantially aligned a single plane.

9. The magnet assembly of claim 6, wherein the first surfaces of the first and second center-adjacent magnets and the first surfaces of the first and second outer magnets are substantially aligned a single plane.

10. The magnet assembly of claim 6, wherein:
the first center-adjacent magnet is a first one of a plurality of first center-adjacent magnets, with each of said plurality of first center-adjacent magnets disposed in the region of the first center-adjacent magnet so as to form a first center-adjacent slice and each of said plurality of first center-adjacent magnets disposed such that the magnetization vectors are oriented in the same direction as the first center-adjacent magnet; and
the second center-adjacent magnet is a first one of a plurality of second center-adjacent magnets, with each of said plurality of second center-adjacent magnets disposed in the region of the second center-adjacent magnet so as to form a second center-adjacent slice and each of said plurality of second center-adjacent magnets disposed such that the magnetization vectors are oriented in the same direction as the second center-adjacent magnet.

11. The magnet assembly of claim 6 wherein:

the first outer magnet is a first one of a plurality of first outer magnets, with each of said plurality of first outer magnets disposed in the region of the first outer magnet so as to form a first outer slice and each of said plurality of first outer magnets disposed such that the magnetization vectors of the plurality of first outer magnets are oriented in the same direction as the first outer magnet; and the second outer magnet is a first one of a plurality of second outer magnets, with each of said plurality of second outer magnets disposed in the region of the second outer magnet so as to form a second outer slice and each of said plurality of second outer magnets disposed such that the magnetization vector of the plurality of second outer magnets are oriented in the same direction as the second outer magnet.

12. The magnet assembly of claim 6, wherein the first magnets, second magnets and first and second outer magnets are disposed in a housing.

13. In a portable measurement device, an array of magnets comprising:

a first magnet having top and bottom surfaces and at least one side surface;

a second magnet having top and bottom surfaces and at least one side surface, said second magnet spaced apart from said first magnet with the top surface of said first magnet and the top surface of said second magnet being substantially in a same plane;

a third magnet having top and bottom surfaces and at least one side surface, said third magnet disposed between the first and second magnets, such that the top surface of said third magnet is in a plane which is different from the plane in which the top surfaces of said first and second magnets lie;

wherein the first, second, and third magnets each have magnetization vectors in a same direction; and fourth and fifth magnets each having top and bottom surfaces and at least one side surface with the top surfaces of said fourth and fifth magnet and the top surfaces of said first and second magnets being substantially in the same plane, said fourth and fifth magnets having magnetization vectors which are in a direction which is orthogonal to the direction of the magnetization vectors of said first, second and third magnets and wherein the direction of the magnetization vector of the fourth magnet is opposite the direction of the magnetization vector of the fifth magnet.

14. The portable measurement device of claim 13, wherein the fourth magnet is further disposed away from the first magnet in the direction of the magnetization vectors of the first, second, and third magnets.

15. The magnet assembly of claim 14, wherein the fourth magnet has a magnetization vector directed towards the plane in which the top surfaces of the said first and second magnets lie.

16. The array of magnets of claim 13 wherein the top surface of said third magnet is in a plane which is below a plane in which the top surfaces of said first and second magnets lie.

17. The array of magnets of claim 13, wherein the first, second, third, fourth and fifth magnets are each provided having a substantially same size and shape.

18. The array of magnets of claim 13, wherein the first, second, third, fourth, and fifth magnets are configured to provide a uniform magnetic field in a region above the top surface of the first, second and third magnets.

19. The array of magnets of claim 18, wherein the uniform magnetic field is located above a central region of the first, second, and third magnets.

20. The array of magnets of claim 13, wherein the first, second, and third magnets each comprise a respective matrix of magnets, wherein each matrix of magnets comprises at least one magnet in an x direction of the matrix and at least one magnet in a y direction of the matrix.

21. The array of magnets of claim 20 wherein each magnet in the matrix of magnets is provided having effectively a rectangular prism shape.

22. The array of magnets of claim 20, wherein each magnet in a matrix of magnets is provided having a cube shape with each side of the cube having a length in the range of about 0.25 inch to about 1 inch.

23. The array of magnets of claim 20 wherein each magnet in a matrix of magnets is provided having a cube shape with each side of the cube having a length in the range of about 0.0625 to 6 inches in size.

24. The array of magnets of claim 20, wherein the first, second, third, fourth, and fifth magnets are disposed within a housing.

* * * * *